(12) United States Patent
Murakami

(10) Patent No.: US 8,068,219 B2
(45) Date of Patent: Nov. 29, 2011

(54) POSITION DETECTOR, POSITION DETECTING METHOD AND ANALYZER

(75) Inventor: Miyuki Murakami, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 12/959,195

(22) Filed: Dec. 2, 2010

(65) Prior Publication Data

US 2011/0075147 A1    Mar. 31, 2011

Related U.S. Application Data

(60) Division of application No. 12/183,473, filed on Jul. 31, 2008, now Pat. No. 7,869,012, which is a continuation of application No. PCT/JP2006/324079, filed on Dec. 1, 2006.

(30) Foreign Application Priority Data

| Jan. 31, 2006 | (JP) | ................................ 2006-023818 |
| Jan. 31, 2006 | (JP) | ................................ 2006-023819 |
| Jan. 31, 2006 | (JP) | ................................ 2006-023820 |

(51) Int. Cl.
  *G01N 21/00* (2006.01)
(52) U.S. Cl. ....................................................... 356/72
(58) Field of Classification Search ........................ None
  See application file for complete search history.

(56) References Cited

U.S. PATENT DOCUMENTS

| 6,195,158 | B1 | 2/2001 | Cadell et al. |
| 6,612,156 | B1 * | 9/2003 | Hakimuddin ................. 73/61.75 |
| 2001/0004285 | A1 | 6/2001 | Cadell et al. |
| 2002/0129649 | A1 | 9/2002 | Kim et al. |
| 2002/0180964 | A1 | 12/2002 | Cadell et al. |
| 2004/0232364 | A1 | 11/2004 | Omatoi |
| 2005/0093211 | A1 * | 5/2005 | Shiraishi et al. ............... 266/170 |
| 2005/0176140 | A1 * | 8/2005 | Benedict et al. ............... 435/366 |
| 2006/0275883 | A1 | 12/2006 | Rathgeber et al. |
| 2007/0002678 | A1 | 1/2007 | Murakami |
| 2007/0264161 | A1 | 11/2007 | Rathgeber |

FOREIGN PATENT DOCUMENTS

| DE | 103 25 307 B3 | 7/2004 |
| JP | 61-026025 | 2/1986 |
| JP | 2000-500578 | 1/2000 |
| JP | 2000-338113 | 12/2000 |
| JP | 2002-116213 | 4/2002 |
| JP | 2005-257406 | 9/2005 |
| WO | WO 97/19340 | 5/1997 |

* cited by examiner

*Primary Examiner* — Tu Nguyen

(74) *Attorney, Agent, or Firm* — Kilpatrick Townsend & Stockton LLP

(57) ABSTRACT

A position detector is for detecting a position of liquid held in a vessel. The position detector includes a sound wave generator disposed in contact with the vessel and having a plurality of sound generating elements for generating a sound wave by electrical energy; and a measuring unit that measures electrical characteristics of each of the sound generating elements based on the electrical energy reflected from each of the sound generating elements. The position detector also includes a determining unit that determines the presence or absence of the liquid at a position of each of the sound generating elements based on difference in the electrical characteristics measured at the measuring unit.

11 Claims, 32 Drawing Sheets

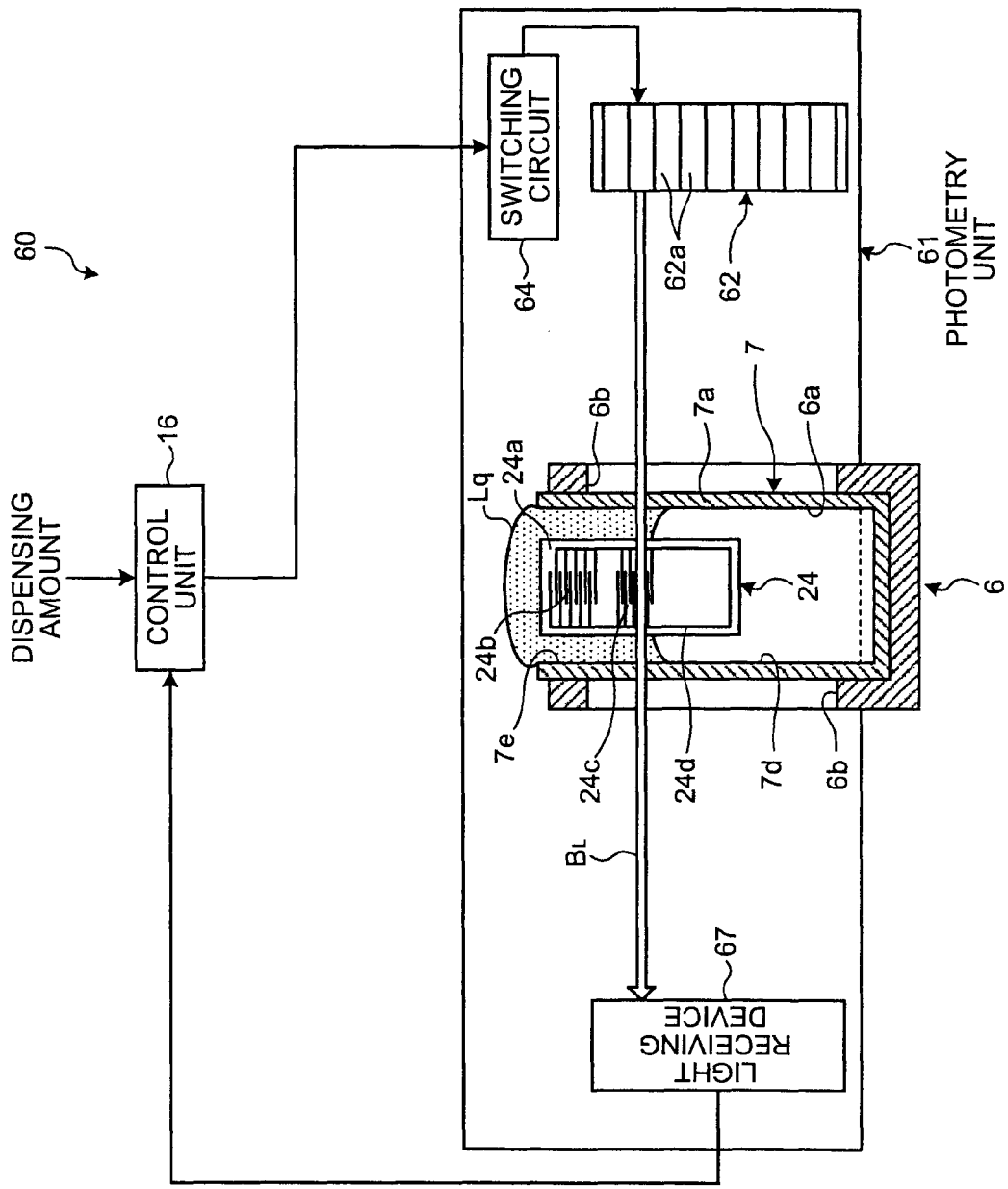

POSITION DETECTOR, POSITION DETECTING METHOD AND ANALYZER

CROSS-REFERENCE TO RELATED APPLICATIONS

This application is a divisional of U.S. application Ser. No. 12/183,473, filed Jul. 31, 2008 which is a continuation of PCT international application Ser. No. PCT/JP2006/324079 filed Dec. 1, 2006 which designates the United States, incorporated herein by reference, and which claims the benefit of priority from Japanese Patent Application Nos. 2006-023818, 2006-023819, and 2006-023820, all filed Jan. 31, 2006, the entire contents of all of which are incorporated herein by reference.

BACKGROUND OF THE INVENTION

1. Field of the Invention

The present invention relates to a position detector, a position detecting method and an analyzer for detecting a position of liquid held in a vessel.

2. Description of the Related Art

Conventionally, the analyzer analyzes constituent concentration or the like of a specimen by measuring optical characteristics of the liquid held in a reaction vessel (for example, see Japanese Patent Application Laid-Open No. 2002-116213).

In the analyzer, when a capacity of the reaction vessel to be used becomes as small as a few nanoliters (nL) to several tens of microliters (μL), an opening through which liquid such as a reagent and a specimen is dispensed becomes relatively narrow relative to the reaction vessel due to downsizing and an effect of surface tension of the liquid becomes extremely large. Therefore, when using the downsized reaction vessel, there has been a case in which in the reaction vessel, the liquid such as the reagent and the specimen is held in the vicinity of the opening and is not introduced to the bottom portion thereof, thus making it impossible to know at which position of the reaction vessel the liquid exists.

SUMMARY OF THE INVENTION

A position detector according to one aspect of the present invention is for detecting a position of liquid held in a vessel. The position detector includes a sound wave generator disposed in contact with the vessel and having a plurality of sound generating elements for generating a sound wave by electrical energy; a measuring unit that measures electrical characteristics of each of the sound generating elements based on the electrical energy reflected from each of the sound generating elements; and a determining unit that determines the presence or absence of the liquid at a position of each of the sound generating elements based on difference in the electrical characteristics measured at the measuring unit.

A position detecting method according to another aspect of the present invention is for detecting a position of liquid held in a vessel. The method includes individually generating a sound wave from each of a plurality of sound generating elements provided on the vessel by electrical energy; measuring electrical characteristics of each of the sound generating elements based on the electrical energy reflected from each of the sound generating elements; and determining a presence or absence of the liquid at a position of each of the sound generating elements based on difference in the measured electrical characteristics to detect a position of the liquid held in the vessel based on the determination of presence or absence of the liquid.

A position detector according to still another aspect of the present invention is for detecting a position of liquid held in a vessel. The position detector includes a plurality of light sources disposed so as to approach the vessel, each light source emitting measurement light for measuring optical characteristics of the liquid; a plurality of light receivers disposed to face the plurality of light sources, respectively, each light receiver receiving the measurement light penetrating the vessel; and a detector that detects a position of the liquid held in the vessel based on photometric data in the light receivers.

An analyzer according to still another aspect of the present invention is for stirring different liquids to react and measuring optical characteristics of reaction liquid to analyze the reaction liquid. The analyzer includes a position detector according to the present invention.

An analyzer according to still another aspect of the present invention is for measuring optical characteristics of liquid. The analyzer includes a vessel for holding the liquid in a state of having at least two gas-liquid interfaces; and a photometric unit that measures the optical characteristics of the liquid held in the vessel.

A vessel according to still another aspect of the present invention is used in an analyzer for measuring optical characteristics of liquid. The vessel includes an opening for introducing the liquid; and a liquid holding section for holding the liquid introduced from the opening in a state of having at least two gas-liquid interfaces.

An analyzer according to still another aspect of the present invention is for measuring optical characteristics of liquid held in a vessel. The analyzer includes a photometric unit that measures the optical characteristics of the liquid; and a control unit that controls a photometric position at which the photometric unit performs photometry of the liquid based on a position at which the liquid is held in the vessel.

A photometric method of an analyzer according to still another aspect of the present invention is for measuring optical characteristics of liquid held in a vessel. The method includes controlling a photometric position at which photometry of the liquid is performed based on a position at which the liquid is held in the vessel; and performing the photometry of the liquid at the controlled photometric position.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 51 is a block diagram schematically showing a second modified example of the automatic analyzer of the sixth embodiment together with the cross-section of the reaction vessel.

DETAILED DESCRIPTION OF THE PREFERRED EMBODIMENTS

Figure 1:
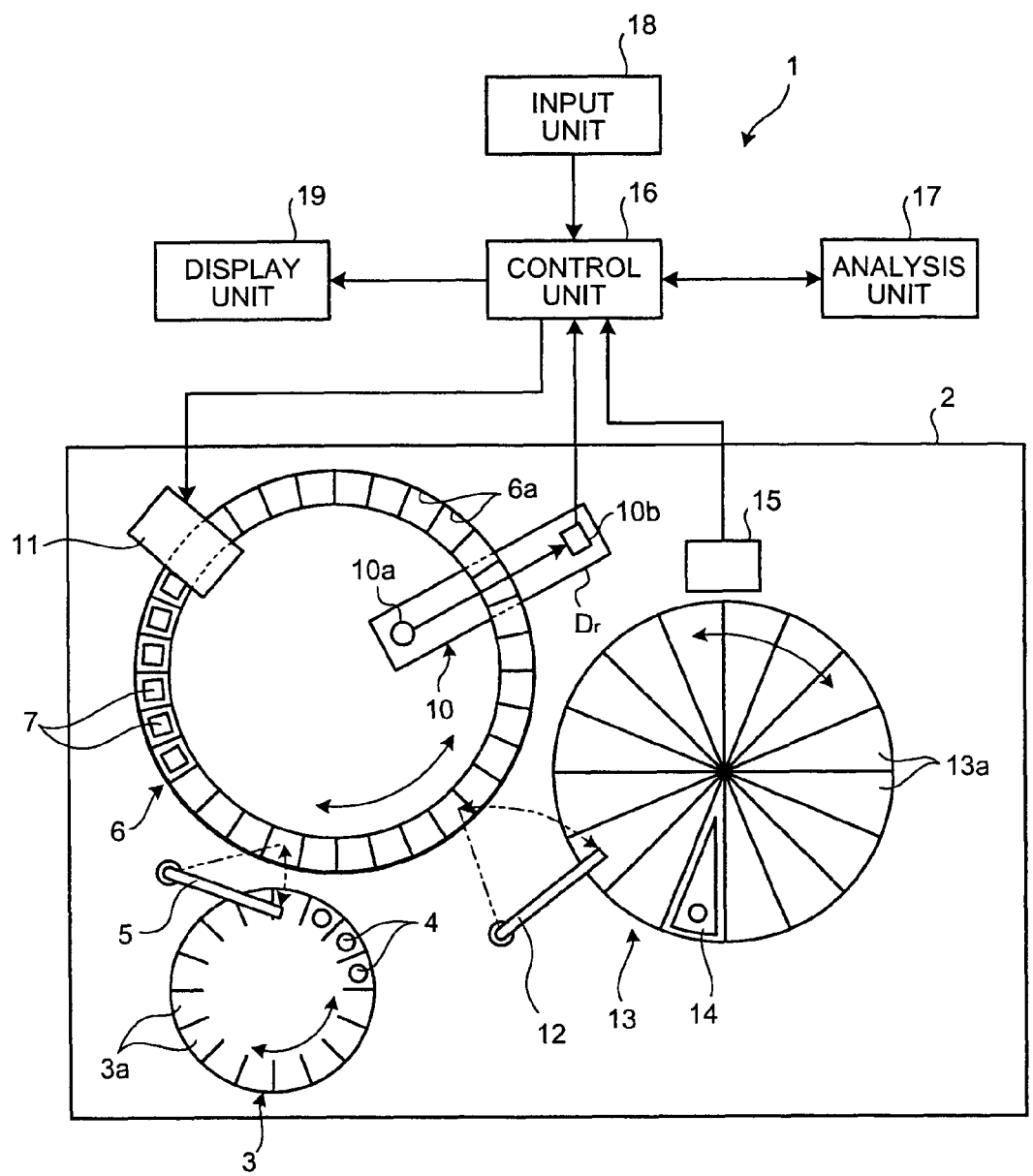
FIG. 1 is a schematic configuration diagram showing an automatic analyzer of a first embodiment.
Figure 2:
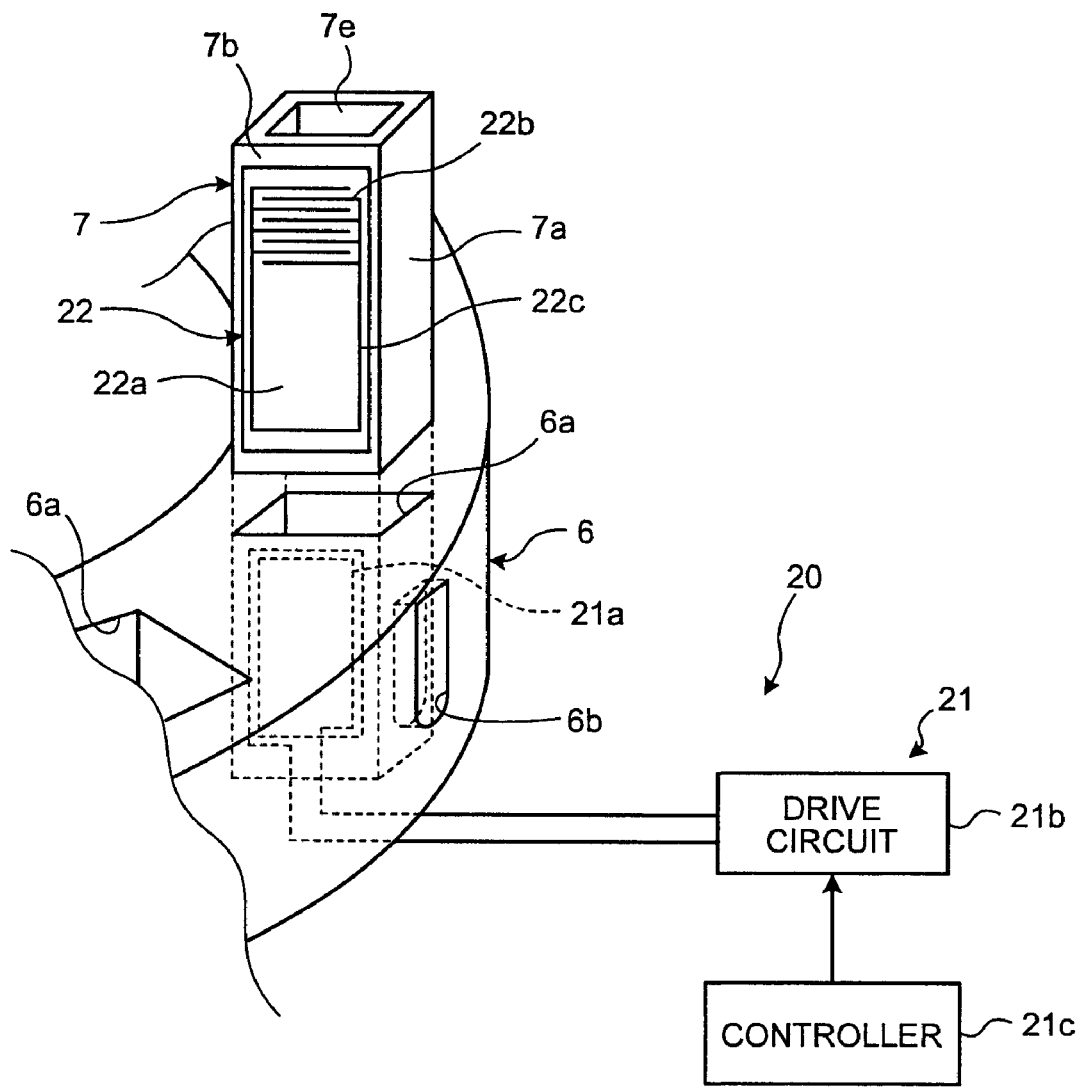
FIG. 2 is a perspective view showing a reaction vessel used in the automatic analyzer of the first embodiment together with a schematic configuration diagram of a part of a reaction wheel and a stirrer.
Figure 3:
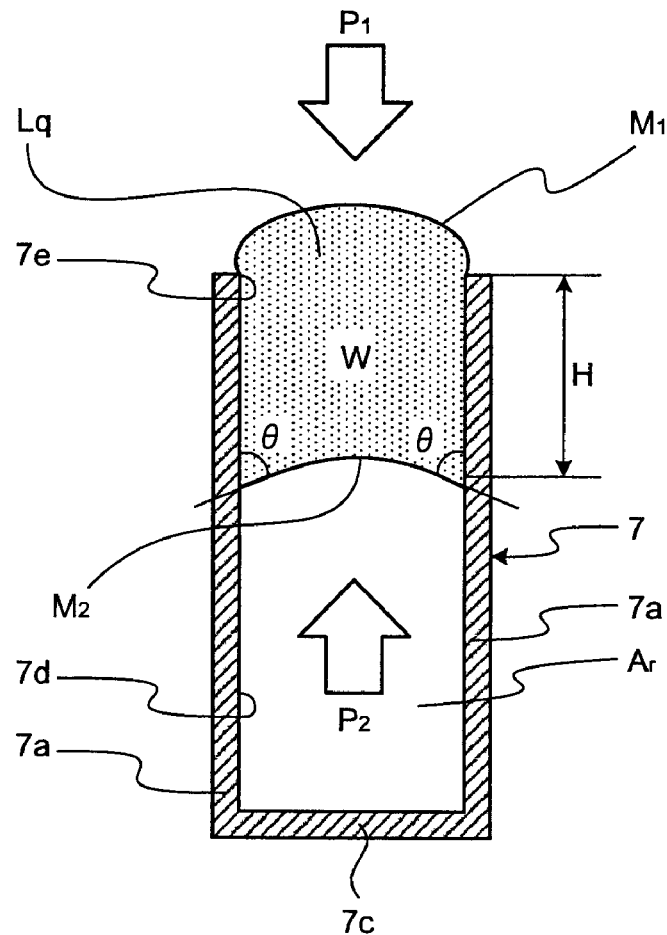
FIG. 3 is a vertical cross-sectional view of the reaction vessel illustrating a relationship among surface tension of held liquid, force acting vertically upward from internal air and gravity of the liquid in the reaction vessel used in the automatic analyzer of the first embodiment.
Figure 4:
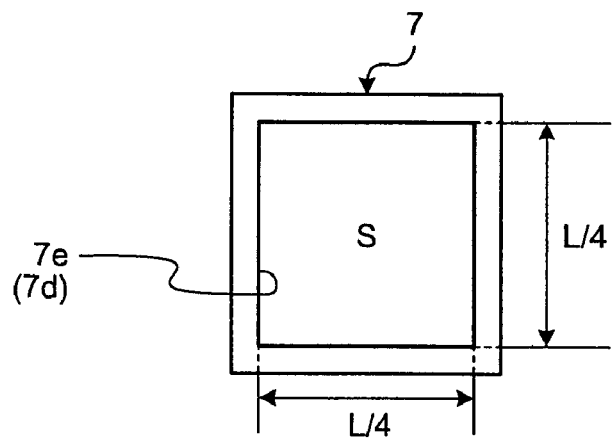
FIG. 4 is a plan view of the reaction vessel of FIG. 3.

Hereinafter, a first embodiment of an analyzer of the present invention will be described in detail with reference to the drawings. FIG. 1 is a schematic configuration diagram showing an automatic analyzer of the first embodiment. FIG. 2 is a perspective view showing a reaction vessel together with a schematic configuration diagram of a part of a reaction wheel and a stirrer. FIG. 3 is a longitudinal sectional view of the reaction vessel illustrating a relationship among surface tension of held liquid, force acting vertically upward from internal air and gravity of the liquid, in the reaction vessel. FIG. 4 is a plan view of the reaction vessel of FIG. 3.

An automatic analyzer 1 is provided with a specimen table 3, a specimen dispensing mechanism 5, a reaction wheel 6, a photometry unit 10, a cleaner 11, a reagent dispensing mechanism 12 and a reagent table 13 on a working table 2, as shown in FIG. 1, and is also provided with a stirrer 20.

The specimen table 3 is rotated in a direction indicated by an arrow by drive means and a plurality of storage chambers 3a arranged at regular intervals along a circumferential direction are provided on an outer circumference thereof, as shown in FIG. 1. A specimen vessel 4 in which the specimen is accommodated is detachably stored in each storage chamber 3a.

The specimen dispensing mechanism 5 is means for dispensing the specimen to a plurality of reaction vessels 7 held on the reaction wheel 6, and as shown in FIG. 1, sequentially dispenses the specimen from a plurality of specimen vessels 4 on the specimen table 3 to the reaction vessels 7. The specimen dispensing mechanism 5 outputs a dispensing amount of the specimen dispensed to the reaction vessels 7 to a control unit 16.

The reaction wheel 6 is rotated in a direction indicated by an arrow by drive means different from that of the specimen table 3 and a plurality of concave portions 6a are provided at regular intervals along a circumferential direction on an outer circumference thereof, as shown in FIG. 1. On the reaction wheel 6, slits 6b (see FIG. 2) through which measurement light passes are formed on both sides in a radial direction of each concave portion 6a. The slit 6b is shaped to have a length substantially corresponding to a vertical direction of a liquid holding section 7d of the reaction vessel 7. The reaction wheel 6 rotates clockwise by (one revolution minus one reaction vessel)/4 per one cycle, and rotates counterclockwise by one concave portion 6a per four cycles. The photometry unit 10 and the cleaner 11 are provided in the vicinity of the reaction wheel 6.

The reaction vessel 7 has a capacity as small as a few nanoliters (nL) to several tens of microliters (μL), and a transparent material, which transmits not less than 80% of light included in analytical light (340 to 800 nm) emitted from a light source 10a of the photometry unit 10, for example, glass including heat-resistant glass and synthetic resin such as cyclic olefin and polystyrene are used. The reaction vessel 7 is a square tubular cuvette in which the liquid holding section 7d having a square horizontal cross section for holding the liquid is formed of side walls 7a and 7b and a bottom wall 7c and having an opening 7e on an upper portion of the liquid holding section 7d, as shown in FIGS. 2 and 4. In the reaction vessel 7, a treatment to impart affinity for liquid such as the specimen and a reagent is applied to an inner surface of the liquid holding section 7d, and two side walls 7a arranged so as to be opposed to each other to transmit the analytical light are used for optical measurement of the liquid. The reaction vessel 7 is arranged in the concave portion 6a such that the side walls 7a are directed to a radial direction of the reaction wheel 6 and the side walls 7b are directed to a circumferential direction of the reaction wheel 6.

Herein, there is used the reaction vessel 7 having an angle of contact with which when liquid Lq is held in a state of having at least two gas-liquid interfaces M1 and M2, as shown in FIGS. 3 and 4, a sum of a volume of a vertical component of surface tension T (F=T·cos θ·L) acting from the held liquid Lq to an entire circumference of an inner wall and force (f=ΔP·S) acting vertically upward from gas, for example, air Ar in the reaction vessel 7 on the liquid Lq, is not smaller than gravity (W=ρ·g·H·S) acting on the liquid Lq as represented by the following equation:

$$F+f=(T\cos\theta\cdot L+\Delta P\cdot S) \geqq W=\rho\cdot g\cdot H\cdot S.$$

At this time, as shown, the angle of contact between the reaction vessel 7 and the held liquid Lq, a length along a circumferential direction in the gas-liquid interface between the liquid Lq and the reaction vessel 7, atmosphere pressure acting on the gas-liquid interface M1, pressure acting from the air Ar in the reaction vessel 7 on the gas-liquid interface M2, density of the liquid Lq, gravity acceleration, a length in a vertical direction of the liquid Lq held in the reaction vessel 7 and a cross-sectional area in a horizontal direction of the liquid holding section 7d are set to θ, L, P1, P2 (ΔP=P1−P2), ρ, g, H and S, respectively. If the reaction vessel 7 has such an angle of contact θ with respect to the liquid Lq, a sum of the surface tension and the pressure of the air Ar is not smaller than the gravity, so that the liquid Lq is held at the opening 7e. Such relationship among the surface tension F, the force f acting on the liquid Lq and the gravity W in the reaction vessel 7 is similarly applied also to another reaction vessel used in each embodiment to be described later, when the air Ar exists in the reaction vessel 7.

The photometry unit 10 is photometric means provided on positions opposed to each other in the radial direction with the concave portion 6a on a lower portion of the reaction wheel 6 interposed therebetween so as to be movable up and down, and has the light source 10a for emitting the analytical light (340 to 800 nm) for analyzing the liquid held in the reaction vessel 7 and a light receiver 10b for dispersing the analytical light, which has penetrated the liquid and receiving the same. A vertical position (photometric position) of the photometry unit 10 is controlled such that the light source 10a and the light receiver 10b move in the vertical direction, which intersects with the gas-liquid interface of the liquid held in the reaction vessel 7, by means of a driver Dr such as a z-axis stage of which operation is controlled by the control unit 16.

The cleaner 11 has discharge means for discharging the liquid and cleaning liquid from the reaction vessel 7 and dispensing means for the cleaning liquid. The cleaner 11 discharges the liquid after photometry from the reaction vessel 7 after the photometry and after that, dispenses the cleaning liquid. A dispensing amount of the cleaning liquid is set to be slightly larger than that of the liquid held in the reaction vessel 7 at the time of the photometry. The cleaner 11 cleans the inside of the reaction vessel 7 by repeating a plurality of times operations of dispensing and discharging the cleaning liquid. The reaction vessel 7 thus cleaned is used again for analyzing a new specimen.

The reagent dispensing mechanism 12 is means for dispensing the reagent to a plurality of reaction vessels 7 held on the reaction wheel 6, and sequentially dispenses the reagent from a predetermined reagent vessel 14 on the reagent table 13, to the reaction vessel 7 as shown in FIG. 1. The reagent dispensing mechanism 12 outputs the dispensing amount of the reagent dispensed to the reaction vessel 7 to the control unit 16 as a dispensing amount signal.

The reagent table 13 is rotated in a direction indicated by an arrow by drive means different from that of the specimen table 3 and of the reaction wheel 6, and a plurality of storage chambers 13a shaped into a fan are provided along the circumferential direction thereof, as shown in FIG. 1. The reagent vessel 14 is detachably stored in each storage chamber 13a. Each of a plurality of reagent vessels 14 is filled with a predetermined reagent according to an inspection item, and a barcode label (not shown) indicating information regarding the accommodated reagent is adhered to an outer surface thereof.

Herein, a reader 15 for reading information such as a kind, a lot, and an expiration date of the reagent recorded on the barcode label adhered to the reaction vessel 14, and outputting the information to the control unit 16 is provided on an outer circumference of the reagent table 13, as shown in FIG. 1.

The control unit 16 is connected to the specimen table 3, the specimen dispensing mechanism 5, the reaction wheel 6, the light receiver 10b, the cleaner 11, the reagent dispensing mechanism 12, the reagent table 13, the reader 15, an analysis unit 17, an input unit 18, a display unit 19 and the stirrer 20, and a microcomputer or the like provided with a storing function for storing an analytical result is used, for example. The control unit 16 controls an operation of each section of the automatic analyzer 1, and based on the information read from the record of the barcode label, if the lot, the expiration date and the like of the reagent are out of a set range, controls the automatic analyzer 1 to stop an analytical operation or alerts an operator.

Also, the control unit 16 obtains in advance a table and a function for deciding the vertical position, that is, the photometric position of the photometry unit 10, based on the dispensing amounts of the specimen and the reagent input from the specimen dispensing mechanism 5 and the reagent dispensing mechanism 12, respectively, and controls operation of the driver Dr driving the photometry unit 10 based on the table and the function, thereby controlling the photometric position. Herein, when a measurement item of the specimen and position information of the reaction vessel 7 are input from the input unit 18, signals corresponding to the input measurement item and the position information of the reaction vessel 7 are output to the control unit 16. The control unit 16 allows the specimen dispensing mechanism 5 and the reagent dispensing mechanism 12 to dispense the specimen and the reagent in a predetermined amount to a specified reaction vessel 7 based on the signals. At this time, as described above, the specimen dispensing mechanism 5 and the reagent dispensing mechanism 12 output the dispensing amount signals regarding the dispensing amounts of the specimen and the reagent dispensed to the reaction vessel 7 to the control unit 16. The control unit 16 outputs the dispensing amount signal to the stirrer 20, and reads the photometric position measured and stored in advance regarding the reaction vessel 7 based on the dispensing amount signal input in this manner, thereby controlling the photometric position of the photometry unit 10 by means of the driver Dr.

The analysis unit 17 is connected to the light receiver 10b through the control unit 16, analyzes a constituent concentration or the like of the specimen from light absorbance of the liquid in the reaction vessel 7 based on an amount of light received by the light receiver 10b, and outputs the analytical result to the control unit 16. The input unit 18 is the section to perform operation of inputting the inspection item or the like to the control unit 16, and a keyboard, a mouse and the like are used, for example. The display unit 19 is for displaying analytical contents and the alert, and a display panel or the like is used.

The stirrer 20 is for driving a surface acoustic wave device 22, and has an electrical power transmitter 21 for transmitting an electrical power to the surface acoustic wave device 22 and the surface acoustic wave device 22, as shown in FIG. 2.

The electrical power transmitter 21 has an RF transmission antenna 21a, a drive circuit 21b and a controller 21c. The electrical power transmitter 21 transmits the electrical power supplied from a high-frequency alternating-current source of about a few MHz to several hundreds of MHz from the RF transmission antenna 21a to the surface acoustic wave device 22 as the drive signal. The RF transmission antenna 21a is attached to an inner surface of the concave portion 6a of the reaction wheel 6. Therefore, the stirrer 20 switches to output the supplied electrical power to a specific RF transmission antenna 21a out of a plurality of RF transmission antennas 21a by turning a switch controlled by the controller 21c, for example.

The drive circuit 21b has an oscillation circuit capable of changing an oscillation frequency based on a control signal from the controller 21c and outputs a high-frequency oscillation signal of about several tens of MHz to several hundreds of MHz to the RF transmission antenna 21a. Herein, the RF transmission antenna 21a and the drive circuit 21b are connected through a contact electrode such that the electrical power is transmitted even when the reaction wheel 6 rotates. The controller 21c controls operation of the drive circuit 21b, and controls, for example, characteristics (frequency, intensity, phase, characteristics of wave), waveforms (sine wave, triangle wave, rectangular wave, burst wave, or the like) or modulations (amplitude modulation, frequency modulation) or the like of a sound wave generated by the surface acoustic wave device 22. Also, the controller 21c may switch the frequency of the oscillation signal oscillated by the drive circuit 21b according to an incorporated timer.

The surface acoustic wave device 22 is stirring means, which receives the drive signal (electrical power) transmitted from the RF transmission antenna 21a to generate the sound wave (surface acoustic wave), thereby stirring the liquid by the generated sound wave. The surface acoustic wave device 22 is attached to the side wall 7a of the reaction vessel 7 through an acoustic matching layer of epoxy resin or the like, as shown in FIG. 2. In the surface acoustic wave device 22, a transducer 22b formed of an interdigital transducer (IDT) and an antenna 22c are formed on a piezoelectric substrate 22a formed of lithium niobate (LiNbO$_3$) or the like. The transducer 22b is a sound generating element for generating the sound wave (surface acoustic wave) by receiving the drive signal (electrical power) transmitted from the RF transmission antenna 21a by the antenna 22c. The surface acoustic wave device 22 avoids the side walls 7a through which the analytical light emitted from the light source 10a of the photometry unit 10 enters or emits and is attached to the side wall 7b adjacent thereto.

The automatic analyzer 1 configured in this manner analyzes the specimen dispensed to the reaction vessel 7 by a photometric method to be described below including a process to control the photometric position at which the photometry of the liquid is performed according to a holding position at which the liquid is held in the reaction vessel 7, and a process to perform the photometry of the liquid at the controlled photometric position.

Figure 5:
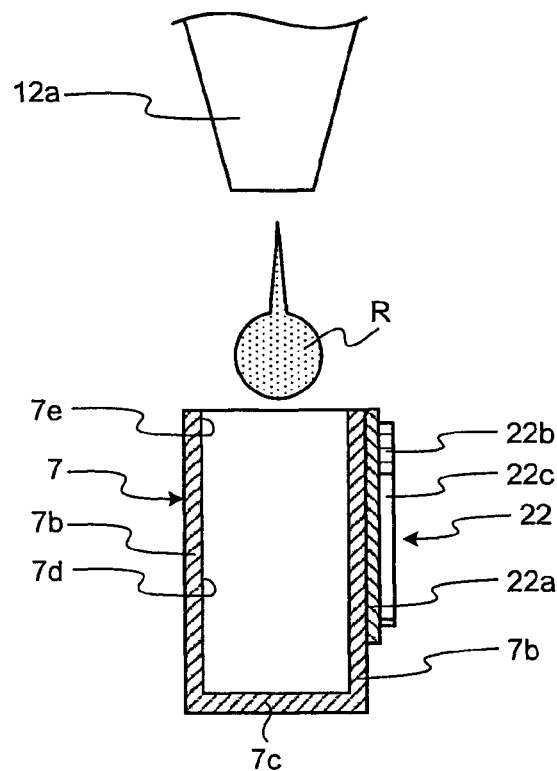
FIG. 5 is a cross-sectional view showing dispensing of a reagent to the reaction vessel by a reagent dispensing mechanism.

First, in the automatic analyzer 1 under the control of the control unit 16, a dispensing nozzle 12a of the reagent dispensing mechanism 12 sequentially dispenses a reagent R from a predetermined reagent vessel 14 of the reagent table 13 to the reaction vessel 7, which comes along the circumferential direction by the rotation of the reaction wheel 6 (see FIG. 5). At this time, the reagent dispensing mechanism 12 outputs the dispensing amount signal regarding the dispensing amount of the reagent dispensed to the reaction vessel 7 to the control unit 16.

Figure 6:
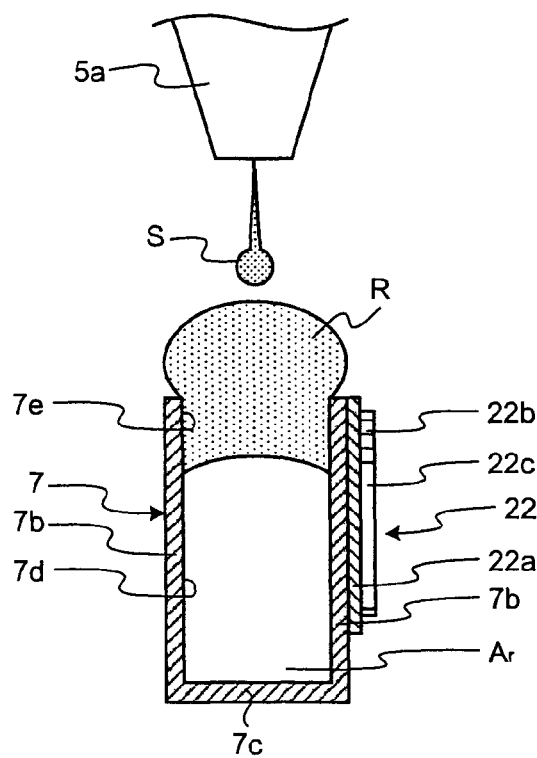
FIG. 6 is a cross-sectional view showing dispensing of a specimen to the reaction vessel of FIG. 5 by a specimen dispensing mechanism.

Then, in the reaction vessel 7, since the capacity thereof is as extremely small as a few nanoliters (nL) to several tens of microliters (μL), the reagent R is held in the vicinity of the opening 7e through the air Ar in a state of downwardly penetrating from the opening 7e, as shown in FIG. 6, according to at least one of a kind or the amount thereof and a form or the material of the reaction vessel 7. That is, since the reaction vessel 7 has the angle of contact θ with which the sum of the volume of the vertical component of the surface tension T ($F=T \cdot \cos \theta \cdot L$) acting from the held reagent R on the entire circumference of the inner wall, and the force ($f=\Delta P \cdot S$) acting vertically upward from the air Ar on the reagent R is not smaller than the gravity ($W=\rho \cdot g \cdot H \cdot S$) acting on the reagent R, the reagent R is held in the vicinity of the opening 7e.

After dispensing the reagent R, the automatic analyzer 1 rotates the reaction wheel 6 under the control of the control unit 16 and moves the reaction vessel 7 to which the reagent R has been dispensed to the vicinity of the specimen dispensing mechanism 5. Next, the automatic analyzer 1 drives the specimen dispensing mechanism 5 under the control of the control unit 16. Thereby, in the reaction vessel 7, a specimen S is dispensed from a predetermined specimen vessel 4 on the reagent R by a dispensing nozzle 5a (see FIG. 6). Mixed liquid Lm of the reagent R and the specimen S is held in the vicinity of the opening 7e for the above-described reason (see FIG. 7).

Figure 7:
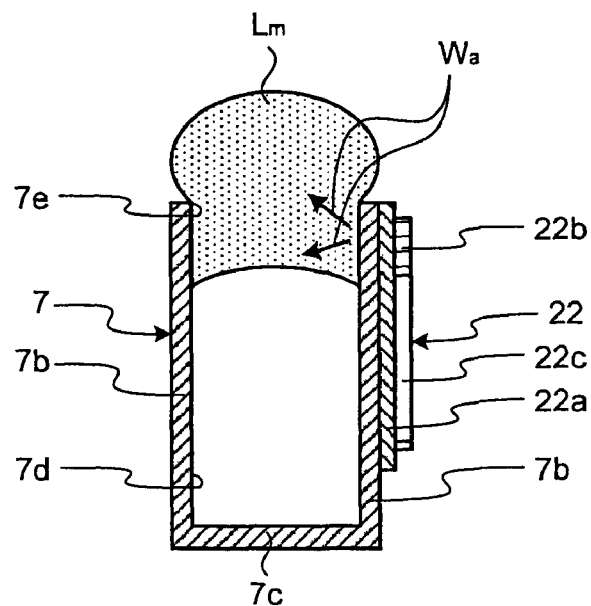
FIG. 7 is a cross-sectional view of the reaction vessel showing a state in which a liquid specimen obtained by mixing the reagent and the specimen is stirred by a sound wave generated by a transducer of a surface acoustic wave device.

At this time, the specimen dispensing mechanism 5 outputs the dispensing amount signal regarding the dispensing amount of the specimen dispensed to the reaction vessel 7 to the control unit 16. Based on the dispensing amount signals regarding the dispensing amount of the reagent and the specimen input in this manner, in the automatic analyzer 1, the control unit 16 reads the photometric position stored in advance, and controls the photometric position of the photometry unit 10 by means of the driver Dr. However, since the mixed liquid Lm of the reagent R and the specimen S is held in the vicinity of the opening 7e of the reaction vessel 7 as shown in FIG. 7, the control unit 16 holds the photometry unit 10 at an initial position thereof near the opening 7e of the reaction vessel 7 and does not change the vertical position thereof.

After dispensing the reagent and the specimen to the reaction vessel 7 in this manner, the automatic analyzer 1 drives the surface acoustic wave device 22 by the driver 20 under the control of the control unit 16. Thereby, in the reaction vessel 7, a sound wave Wa generated by the transducer 22b, which is the sound generating element, leaks to the mixed liquid Lm as shown in FIG. 7, and the mixed liquid Lm is stirred by the leaked sound wave Wa. As a result, in the mixed liquid Lm, the reagent R and the specimen S react with each other.

Figure 8:
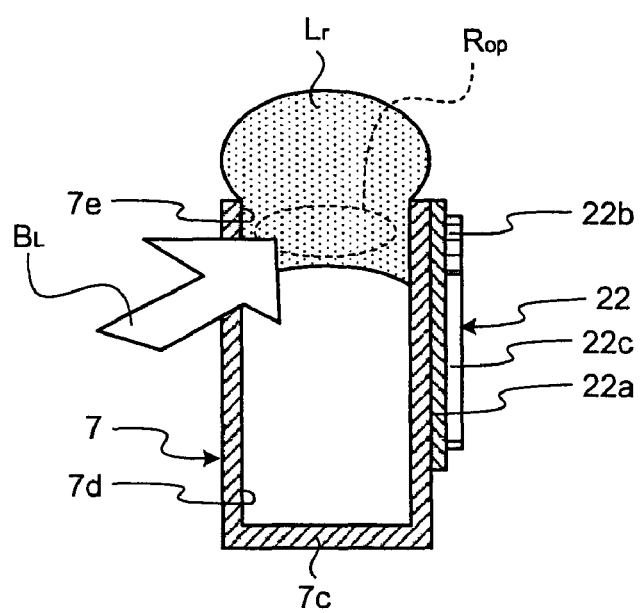
FIG. 8 is a cross-sectional view of the reaction vessel showing a state in which photometry of reaction liquid of the reagent and the specimen is performed by a bundle of light emitted from a light source at an initial position of a photometry unit.

The automatic analyzer 1 allows the reagent R and the specimen S to react in this manner, thereby making reaction liquid Lr (see FIG. 8), and after that, moves the reaction vessel 7 holding the reaction liquid by rotating the reaction wheel 6 under the control of the control unit 16. Thereby, in the reaction vessel 7, when this passes through the photometry unit 10, the photometry of the reaction liquid Lr held in the vicinity of the opening 7e is performed at the initial position of the photometry unit 10 by a bundle of light BL emitted from the light source 10a, as shown in FIG. 8. Herein, a portion indicated by a broken line in FIG. 8 is a photometry area Rop. Meanwhile, as the bundle of light shown in FIG. 8, the one having an oval shape at a cross section orthogonal to the moving direction is used.

Figure 9:
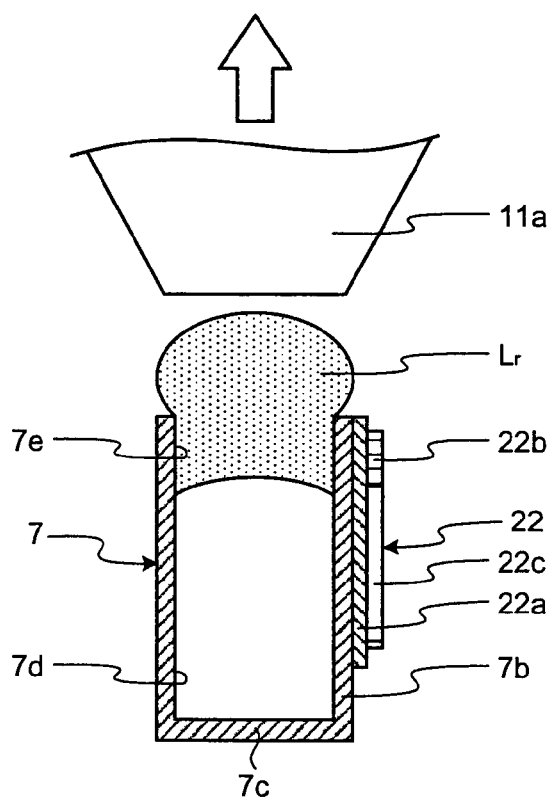
FIG. 9 is a cross-sectional view of the reaction vessel showing a state in which the reaction liquid after the photometry is sucked by a sucking nozzle of a cleaner from the reaction vessel after the photometry.
Figure 10:
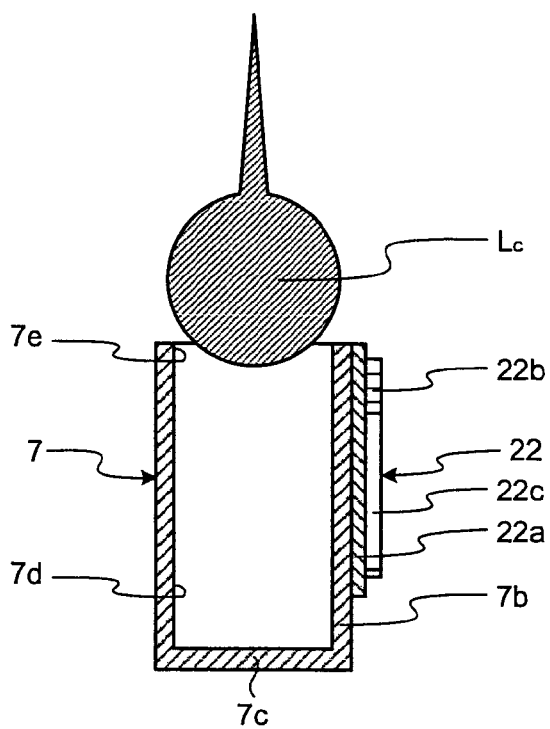
FIG. 10 is a cross-sectional view of the reaction vessel showing a state in which a cleaning liquid is dispensed to the reaction vessel from which the reaction liquid has been sucked.

After the photometry, the automatic analyzer 1 drives the cleaner 11 under the control of the control unit 16, and sucks the reaction liquid Lr after the photometry from the reaction vessel 7 after the photometry by a suction nozzle 11a, as shown in FIG. 9. Next, the automatic analyzer 1 discharges cleaning liquid Lc from a cleaning nozzle of the cleaner 11 to the reaction vessel 7, as shown in FIG. 10, under the control of the control unit 16. An amount of the cleaning liquid Lc to be discharged is set slightly larger than that of the reaction liquid Lr, and this is discharged several times so as not to be accumulated at the opening 7e. In a case in which the cleaning liquid Lc accumulates so as to block the opening 7e, the surface acoustic wave device 22 is driven and the cleaning liquid Lc is sent to the liquid holding section 7d by utilizing the generated sound wave for cleaning the liquid holding section 7d.

Figure 11:
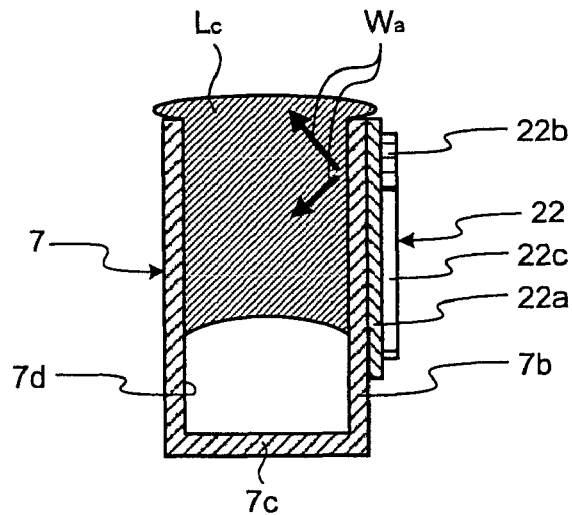
FIG. 11 is a cross-sectional view of the reaction vessel showing a state in which the dispensed cleaning liquid is stirred by the sound wave generated by the transducer of the surface acoustic wave device to clean the reaction vessel.
Figure 12:
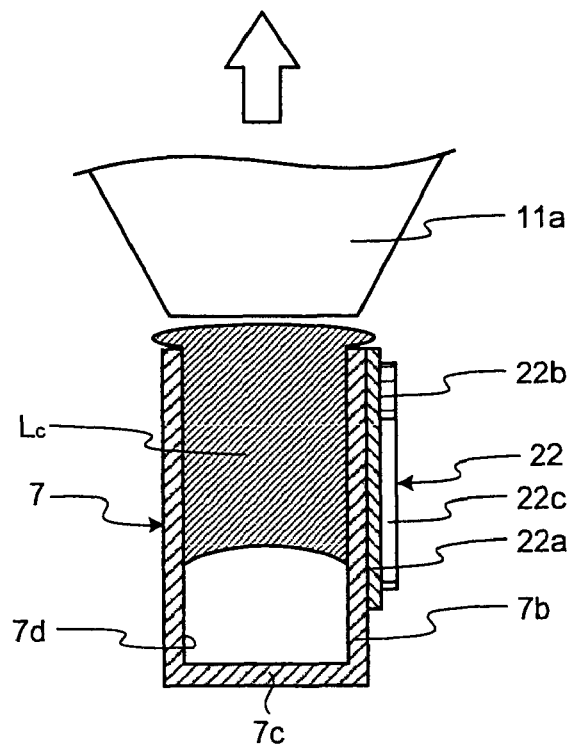
FIG. 12 is a cross-sectional view of the reaction vessel showing a state in which the cleaning liquid, which has cleaned the reaction vessel, is sucked by the sucking nozzle of the cleaner.

Next, the automatic analyzer 1 drives the surface acoustic wave device 22 by the driver 20 under the control of the control unit 16. Thereby, the reaction vessel 7 stirs the cleaning liquid Lc by the sound wave Wa leaking into the cleaning liquid Lc, as shown in FIG. 11, as in the case in which the reagent R and the specimen S react with each other, and cleans the liquid holding section 7d by the cleaning liquid Lc. After cleaning the reaction vessel 7, the automatic analyzer 1 drives the cleaner 11 under the control of the control unit 16, and sucks the cleaning liquid Lc, which has cleaned the liquid holding section 7d, by the suction nozzle 11a, as shown in FIG. 12. The automatic analyzer 1 cleans the reaction vessel 7 by allowing the cleaner 11 to repeat a plurality of times a series of operations of discharging, stirring and sucking of the cleaning liquid Lc under the control of the control unit 16. The reaction vessel 7 cleaned in this manner is used again for analyzing the new specimen.

In such a manner, when the capacity of the reaction vessel 7 becomes as extremely small as a few nanoliters (nL) to several tens of microliters (μL), the liquid is held in the vicinity of the opening 7e due to a large effect of the surface tension. Therefore, in a case in which the liquid is held in the vicinity of the opening 7e, it is reasonable to perform the photometry in this state, since extra energy for sending the liquid to inside the reaction vessel 7 is not wasted.

Figure 13:
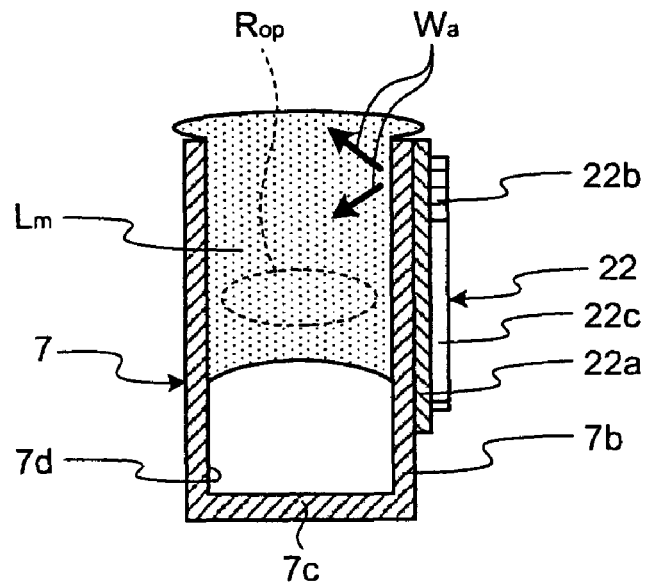
FIG. 13 is a cross-sectional view of the reaction vessel illustrating stirring of the liquid specimen and control of the photometric position in a case in which an amount of the liquid specimen is large.

However, the position at which the reaction vessel 7 holds the liquid including the reagent R and the specimen S varies according to at least one of the kind or the amount of the liquid and the form or the material of the reaction vessel 7. Therefore, for example, in a case in which the dispensing amounts of the reagent and the specimen are large and the amount of the mixed liquid Lm is large, as shown in FIG. 13, the control unit 16 first drives the surface acoustic wave device 22 and stirs the mixed liquid Lm by the sound wave Wa to allow the reagent R and the specimen S to react with each other.

After that, the control unit 16 may perform the photometry of the reaction liquid at the initial position of the photometry unit 10 without controlling the photometric position, or may perform the photometry of the reaction liquid after controlling the photometric position. In this case, the control unit 16 reads the photometric position stored in advance based on the dispensing amount signals regarding the dispensing amounts of the specimen and the reagent input from the specimen dispensing mechanism 5 and the reagent dispensing mechanism 12, respectively, moves (lowers) the photometry unit 10 from the initial position thereof to a central portion in the vertical direction of the reaction vessel 7 by means of the driver Dr, thereby controlling the photometric position. Therefore, in the reaction vessel 7, the photometry of the held reaction liquid is performed at the photometric area Rop, which has moved downward.

Figure 14:
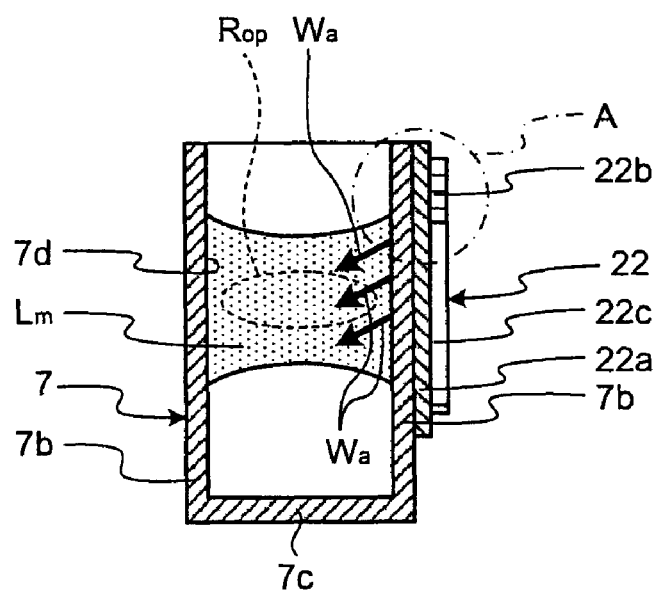
FIG. 14 is a cross-sectional view of the reaction vessel illustrating stirring of the liquid specimen and control of the photometric position in a case in which a holding position of the liquid specimen is different.
Figure 15:
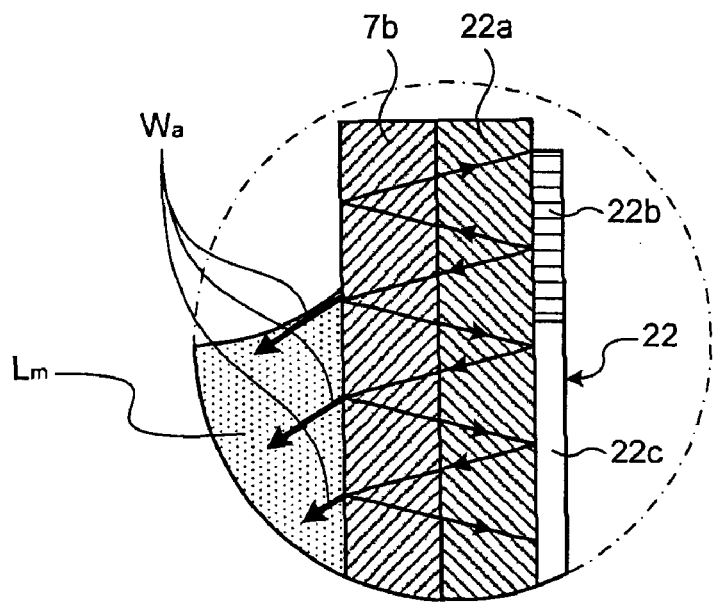
FIG. 15 is an enlarged view of a portion A of FIG. 14.

On the other hand, there is a case in which the mixed liquid Lm intrudes into the central portion in the vertical direction of the reaction vessel 7, and is held at the position distant from the transducer 22b of the surface acoustic wave device 22, as shown in FIG. 14, even though the amount thereof is small, for example, due to extremely small surface tension or large density $\rho$. In such a case, the sound wave Wa generated by the transducer 22b is not radiated in the air of which acoustic impedance largely differs from that of the material of the reaction vessel 7. Therefore, the sound wave Wa is propagated through the piezoelectric substrate 22a and the side wall 7b and is radiated in the mixed liquid Lm at the portion of the mixed liquid Lm at which the difference in acoustic impedance is small, as shown in FIG. 15. In this manner, the mixed liquid Lm is stirred by an acoustic flow generated by the sound wave Wa radiated in the mixed liquid Lm and the specimen and the reagent react with each other, thereby the reaction liquid is obtained.

After that, the control unit 16 reads the photometric position stored in advance based on the dispensing amount signals regarding the dispensing amounts of the specimen and the reagent input from the specimen dispensing mechanism 5 and the reagent dispensing mechanism 12, respectively, lowers the photometry unit 10 from the initial position thereof to central portion in the vertical direction of the reaction vessel 7 by means of the driver Dr, thereby controlling the photometric position. Thereby, the automatic analyzer 1 may perform the photometry of the reaction liquid at the photometric area Rop (see FIG. 14) at which the reaction liquid of the reaction vessel 7 exists.

Figure 16:
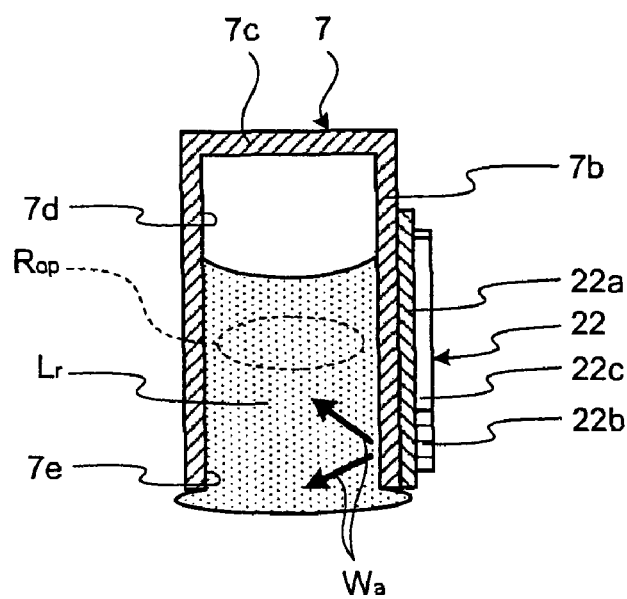
FIG. 16 is a cross-sectional view of the reaction vessel illustrating stirring of the liquid specimen and control of the photometric position in a case in which an arrangement of the reaction vessel is different.

Also, since the capacity of the reaction vessel 7 is as small as a few nanoliters (nL) to several tens, of microliters (μL), the effect of the surface tension of the liquid is larger than that of the gravity acting on the held liquid. Therefore, the reaction vessel 7 may be arranged in the concave portion 6a of the reaction wheel 6 such that the opening 7e is directed vertically downward, as shown in FIG. 16. When thus configured, the control unit 16 reads the photometric position stored in advance based on the dispensing amount signals regarding the dispensing amounts of the specimen and the reagent input from the specimen dispensing mechanism 5 and the reagent dispensing mechanism 12, respectively, and lowers the photometry unit 10 from the initial position thereof to the central portion in the vertical direction of the reaction vessel 7 by means of the driver Dr, thereby controlling the photometric position. By controlling in such a manner, the automatic analyzer 1 may perform the photometry of the reaction liquid Lr at the photometric area Rop (see FIG. 16) at which the reaction liquid Lr of the reaction vessel 7 exists. Also, as another alternative embodiment, the reaction vessel 7 may be arranged in a horizontal direction. In this case, since the gas-liquid interfaces align in the horizontal direction, the photometric position of the photometry unit 10 is controlled between the two gas-liquid interfaces. That is, the photometric position is controlled in the horizontal direction.

Herein, the reaction vessel has only to have the opening for introducing the liquid and the liquid holding section for holding the liquid in a state of having at least two gas-liquid interfaces. Therefore, as a reaction vessel 8 shown in FIGS. 17 and 18, the reaction vessel may be formed such that a liquid holding section 8d for holding the liquid is formed of a pair of side walls 8a arranged so as to face each other in parallel, a pair of inclined walls 8b arranged so as to face each other and become narrower in a downward direction and a bottom wall 8c, and an opening 8e is provided on an upper portion of the liquid holding section 8d. At this time, the reaction vessel 8 is formed of the same material as that of the reaction vessel 7, the treatment to impart affinity for liquid such as the specimen and the reagent is applied to the inner surface thereof, and the capacity thereof is as small as that of the reaction vessel 7. In the reaction vessel 8, the surface acoustic wave device 22 is attached to the inclined walls 8b and a pair of side walls 8a is used for optically measuring the liquid. The reaction vessel 7 is arranged in the concave portion 6a such that the side walls 8a are directed in the radial direction of the reaction wheel 6 and the inclined walls 8b are directed in the circumference direction of the reaction wheel 6.

Figure 18:
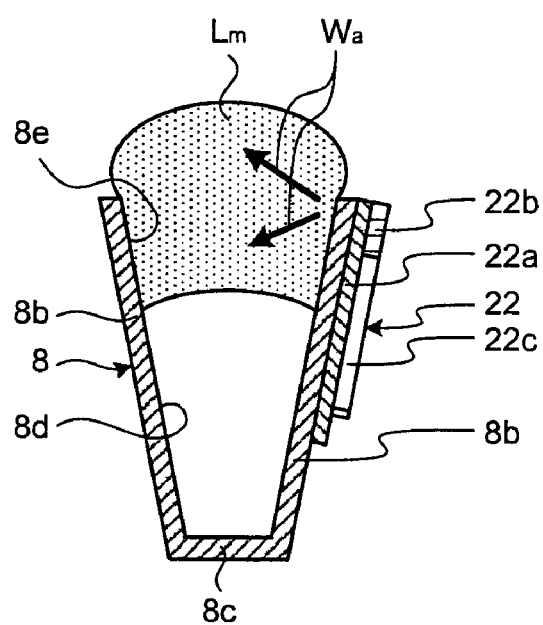
FIG. 18 is a cross-sectional view of the reaction vessel shown in FIG. 17.

In the reaction vessel 8, the liquid dispensed from above is held in the vicinity of the opening 8e by the effect of the surface tension as in the reaction vessel 7. Therefore, the reaction vessel 8 stirs the mixed liquid Lm of the reagent R and the specimen S by the sound wave Wa generated by the surface acoustic wave device 22 in the vicinity of the opening 8e, as shown in FIG. 18, and the photometry of the reaction liquid is performed in the vicinity of the opening 8e. However, the position at which the reaction vessel 8 holds the liquid including the reagent R and the specimen S varies according to at least one of the kind or the amount of the liquid and the form or the material of the reaction vessel 8. Therefore, the control unit 16 may read the photometric position stored in advance based on the dispensing amount signals regarding the dispensing amounts of the specimen and the reagent input from the specimen dispensing mechanism 5 and the reagent dispensing mechanism 12, respectively, and control the photometric position of the photometry unit 10 by means of the driver Dr.

Figure 19:
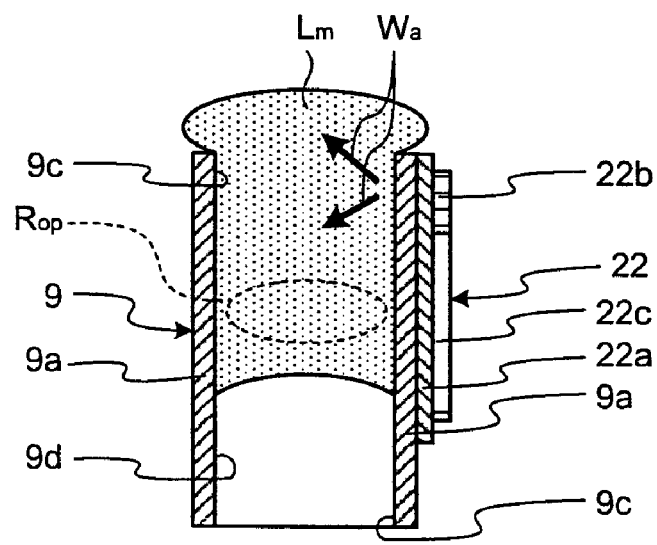
FIG. 19 is a cross-sectional view showing a second modified example of the reaction vessel.

Also, the reaction vessel may form a liquid holding section 9d having openings 9c in upper and lower portions by two pairs of side walls 9a arranged so as to face each other in parallel, as in the reaction vessel 9 shown in FIG. 19. At this time, the reaction vessel 9 is formed of the same material as that of the reaction vessel 7, the treatment to impart affinity for liquid such as the specimen and the reagent is applied to the inner surface thereof, and the capacity thereof is as small as that of the reaction vessel 7.

Therefore, in the reaction vessel 9, the liquid dispensed from above is held in the vicinity of the opening 9c due to the effect of the surface tension as in the reaction vessel 7. Therefore, the reaction vessel 9 may stir the mixed liquid Lm of the reagent R and the specimen S by the sound wave Wa generated by the surface acoustic wave device 22 in the vicinity of the opening 9c, as shown in FIG. 19, and perform the photometry of the reaction liquid obtained by reacting the reagent R and the specimen S in the vicinity of the opening 9c. However, the position at which the reaction vessel 9 holds the liquid including the reagent R and the specimen S varies depending on at least one of the kind or the amount of the liquid and the form or the material of the reaction vessel 9. Therefore, in such a case, the control unit 16 my read the photometric position stored in advance based on the dispensing amount signals regarding the dispensing amounts of the specimen and the reagent input from the specimen dispensing mechanism 5 and the reagent dispensing mechanism 12, respectively, and control the photometric position by the photometry unit 10 by means of the driver Dr.

Figure 20:
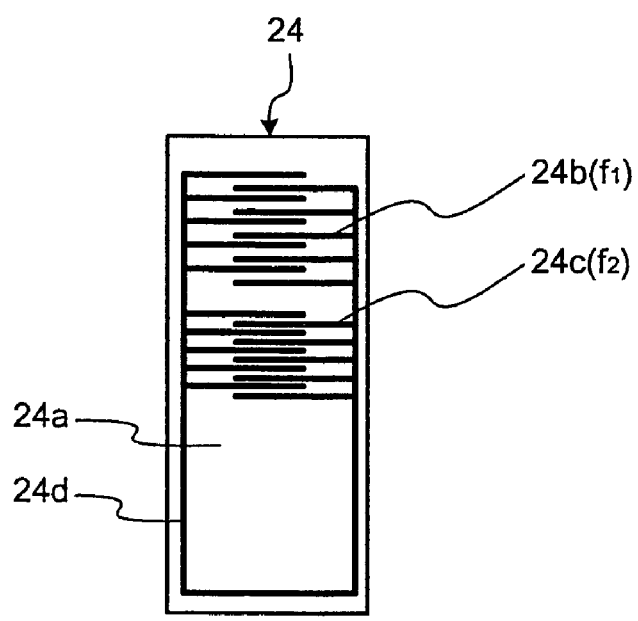
FIG. 20 is a front view showing a modified example of the surface acoustic wave device.
Figure 21:
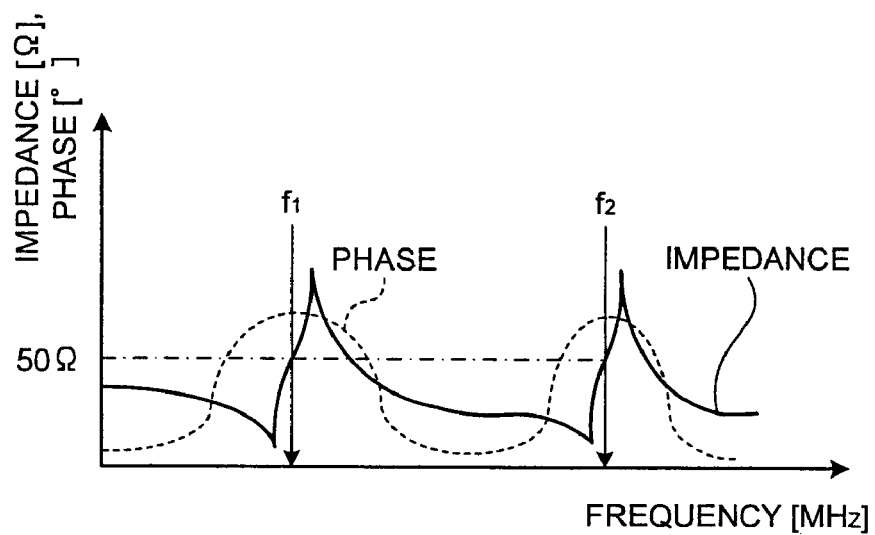
FIG. 21 is a frequency characteristic diagram of impedance and phase of the surface acoustic wave device shown in FIG. 20.

On the other hand, the surface acoustic wave device may be configured such that two transducers 24b and 24c each formed of the interdigital transducer (IDT) are formed on a piezoelectric substrate 24a formed of the same material as that of the piezoelectric substrate 22a and the transducers 24b and 24c are parallelly connected by an antenna 24d, as in the surface acoustic wave device 24 shown in FIG. 20. At this time, the transducers 24b and 24c of which impedance and phase relative to a drive frequency have frequency characteristics shown in FIG. 21 are used, and the center frequency of the transducer 24b located on an upper portion is set to f1 and the center frequency of the transducer 24c located on a lower portion is set to f2 (>f1). Also, the surface acoustic wave device 24 is attached to the side wall 7b of the reaction vessel 7 through an acoustic matching layer in a state in which the transducer 24b is located on the upper portion.

Therefore, in the surface acoustic wave device 24, when the drive signal of the frequency f1 is transmitted from the RF transmission antenna 21a of the electrical power transmitter 21, the transducer 24b located on the upper portion is excited, and when the drive signal of the frequency f2 is transmitted, the transducer 24c located on the lower portion is excited.

Therefore, in the automatic analyzer 1, the stirrer 20 outputs the drive signal of the frequency f1 from the controller 21c to the surface acoustic wave device 24 under the control of the control unit 16, for example, in a case in which the amount of the mixed liquid of the reagent and the specimen is small and this liquid is held in the vicinity of the opening 7e on the upper side of the liquid holding section 7d by the dispensing amount signals output from the control unit 16 to the stirrer 20. Then, in the automatic analyzer 1, the drive signal of the frequency f1 is transmitted from the RF transmission antenna 21a to the surface acoustic wave device 24 when the reaction wheel 6 stops.

Figure 22:
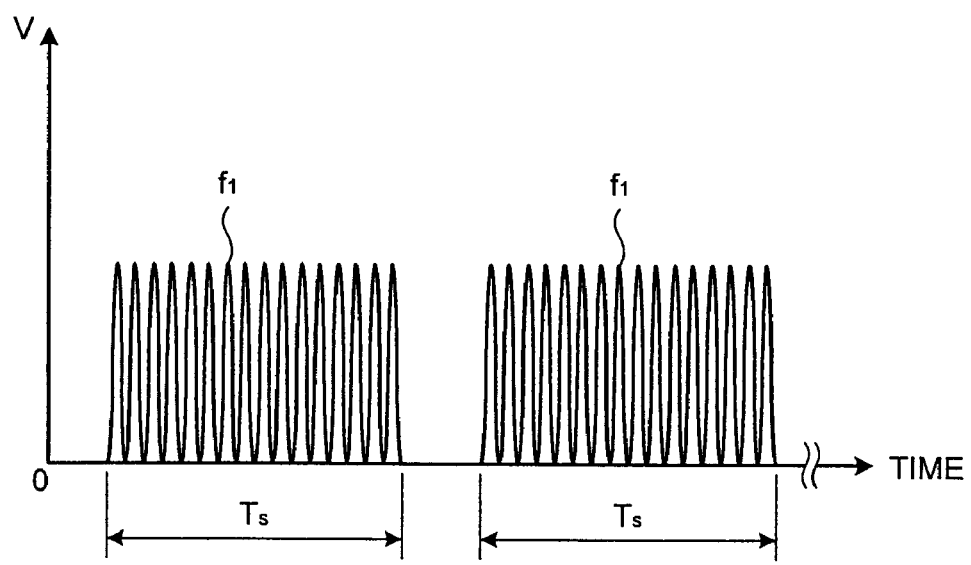
FIG. 22 is a view showing a first drive example of the surface acoustic wave device shown in FIG. 20.
Figure 23:
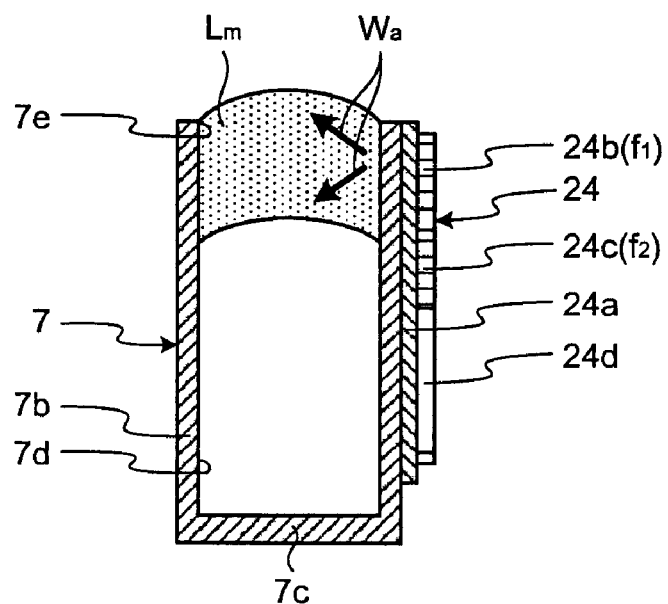
FIG. 23 is a cross-sectional view of the reaction vessel showing a state in which the sound wave generated by the transducer of the surface acoustic wave device driven in the first drive example leaks into the liquid held in the vicinity of the opening of the liquid holding section.

Thereby, in the stirrer 20, the transducer 24b located on the upper side of the surface acoustic wave device 24 is sequentially driven by the drive signal of the frequency f during a stopping time Ts in which the reaction wheel 6 stops, as shown in FIG. 22. As a result, the surface acoustic wave (sound wave) induced by the transducer 24b while the reaction wheel 6 is stopped propagates within the side wall 7b of the reaction vessel 7, and the sound wave Wa leaks into the mixed liquid Lm of which acoustic impedance is closer, as shown in FIG. 23. The acoustic flow is generated by the leaked sound wave Wa, and the reagent, and the specimen in the mixed liquid Lm are stirred. After stirring, the control unit 16 performs the photometry of the reaction liquid at the initial position (in the vicinity of the opening 7e) of the photometry unit 10 without controlling the photometric position.

On the other hand, by the dispensing amount signals output from the control unit 16 to the stirrer 20, for example, in a case in which the amount of the mixed liquid of the reagent and the specimen held in the vicinity of the opening 7e of the liquid holding section 7d is large, the stirrer 20 time-sharingly and alternately outputs the drive signal of the frequency f1 and the drive signal of the frequency f2 from the controller 21c to the surface acoustic wave device 24 under the control of the control unit 16. Then, in the automatic analyzer 1, when the reaction wheel 6 stops, the drive signal of the frequency f1 and the drive signal of the frequency f2 are alternately transmitted from the RF transmission antenna 21a to the surface acoustic wave device 24.

Figure 24:
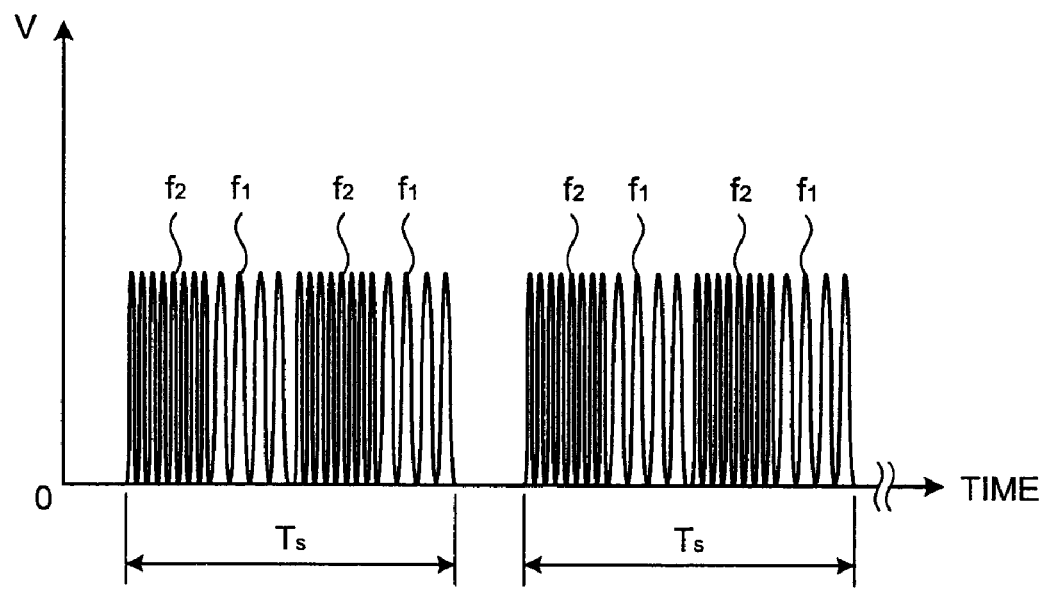
FIG. 24 is a view showing a second drive example of the surface acoustic wave device shown in FIG. 20.

Thereby, in the stirrer 20, the drive signal of the frequency f1 and that of the frequency f2 are alternately input to the surface acoustic wave device 24 during the stopping time Ts in which the reaction wheel 6 stops as shown in FIG. 24. Therefore, every time the reaction wheel 6 of the automatic analyzer 1 stops, the drive signals input to the surface acoustic wave device 24 are alternately changed between that of the frequency f1 and that of the frequency f2, and the transducers 24b and 24c generating the sound wave are self-selectively switched.

Figure 25:
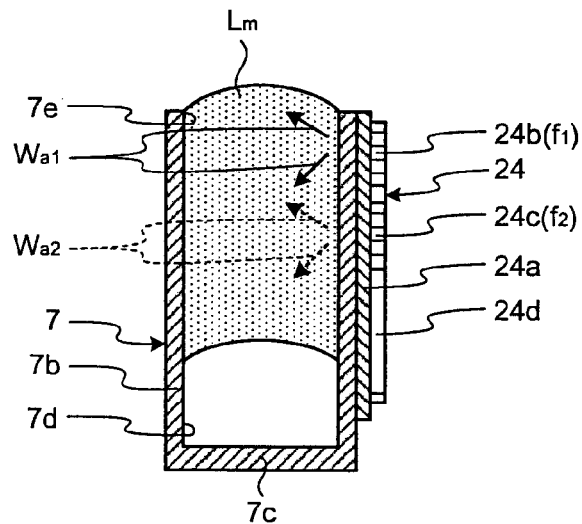
FIG. 25 is a cross-sectional view of the reaction vessel showing a state in which the sound wave generated by the transducer of the surface acoustic wave device driven in the second drive example leaks into the liquid held in the vicinity of the opening of the liquid holding section.

As a result, in the stirrer 20, a sound wave Wa1 of the frequency f1 and a sound wave Wa2 of the frequency f2 alternately leak from the transducer 24b located on the upper side and from the transducer 24c located on the lower side, respectively, into the mixed liquid Lm and the acoustic flow is generated, as shown in FIG. 25. Therefore, the mixed liquid Lm of the reagent and the specimen held in the reaction vessel 7 is efficiently stirred from the bottom portion of the reaction vessel 7 to the gas-liquid interface while minimizing waste of energy, so that sufficient reaction of the reagent and the specimen is assured. In this case, the control unit 16 may perform the photometry of the reaction liquid at the initial position (in the vicinity of the opening 7e) of the photometry unit 10 without controlling the photometric position, or may perform the photometry of the reaction liquid after controlling the photometric position by moving downward the photometry unit 10 from the initial position thereof along the vertical direction of the reaction vessel 7. Meanwhile, a switching time of the frequencies f1 and f2 is not necessarily 1:1, and may be appropriately set and changed according to nature or the liquid amount of the specimen.

Figure 26:
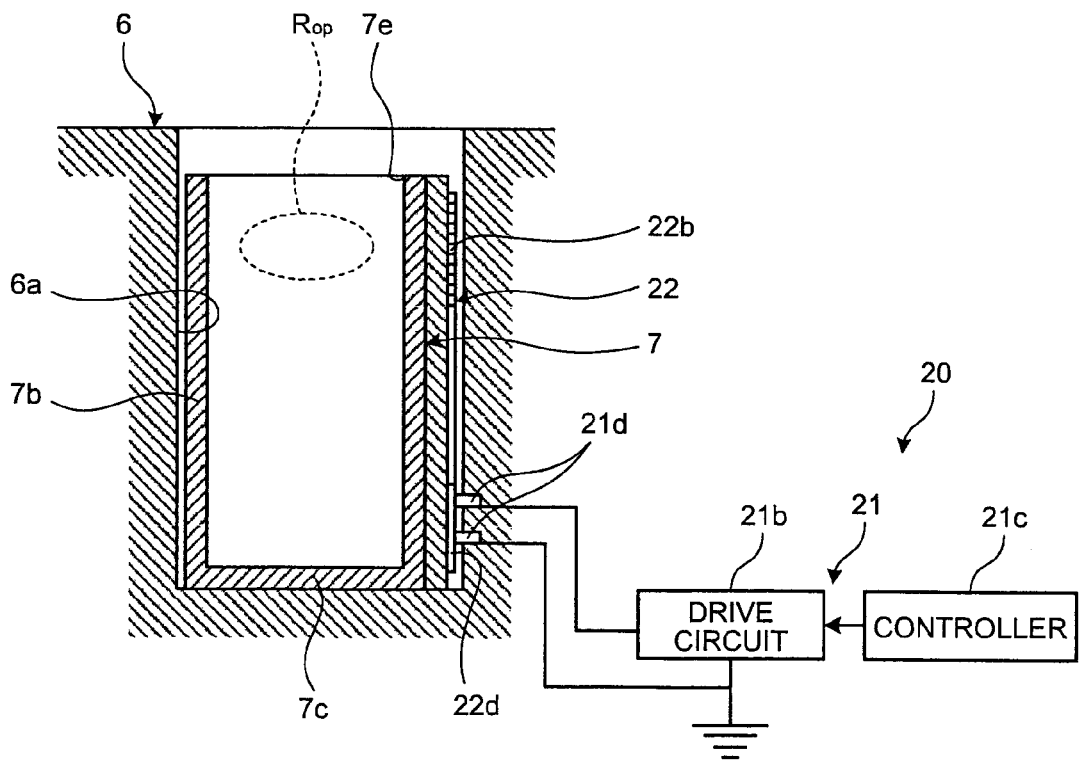
FIG. 26 is a cross-sectional view of a concave portion of a reaction wheel showing a modified example to supply the electrical power to the surface acoustic wave device by a contact together with a schematic configuration diagram of a stirrer.
Figure 27:
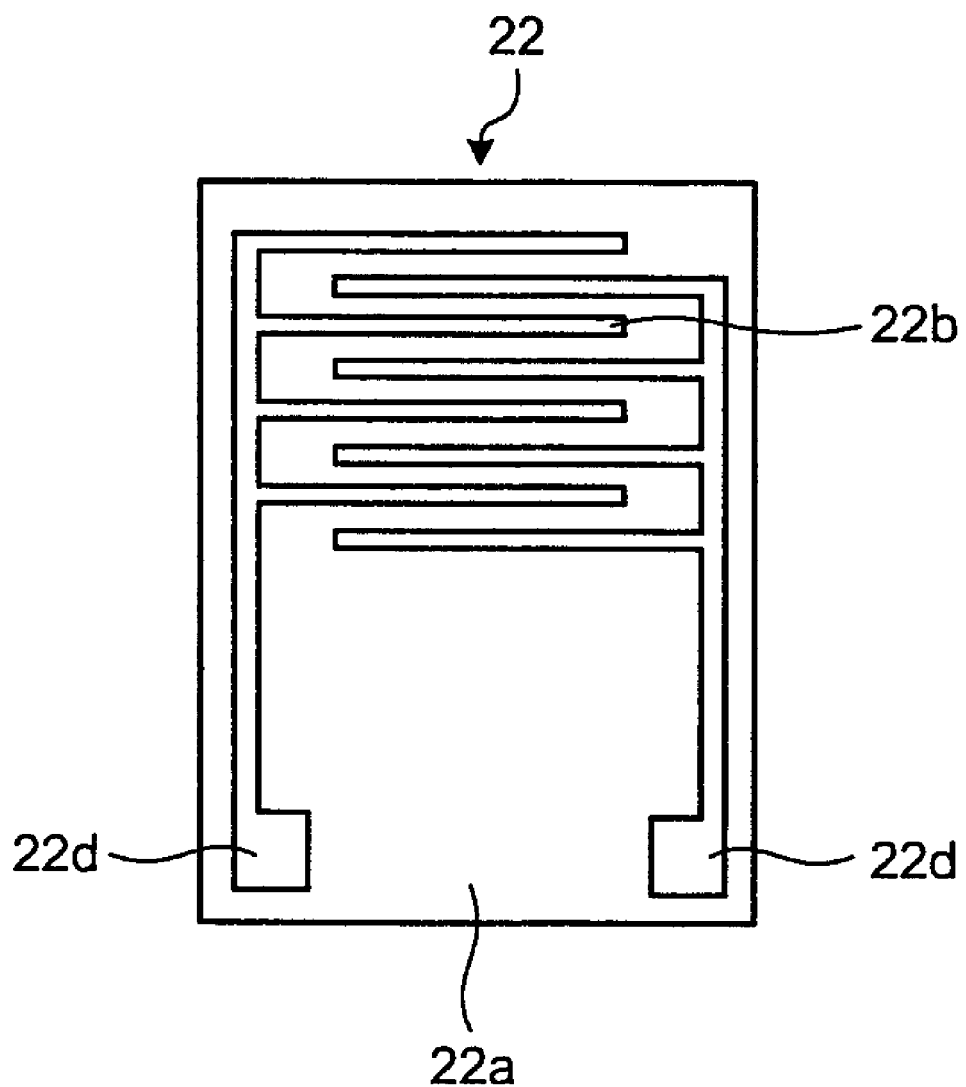
FIG. 27 is a front view of the surface acoustic wave device used in the modified example shown in FIG. 26.

Also, the automatic analyzer 1 of the first embodiment may be configured to supply the electrical power from the driver 20 to the surface acoustic wave device 22 through a fixed line by a contact pin 21d provided on the inner surface of the concave portion 6a of the reaction wheel 6, as shown in FIG. 26. At this time, the surface acoustic wave device 22 forms a contact pad 22d contacting the contact pin 21d in place of the antenna 22c formed on the piezoelectric substrate 22a, as shown in FIG. 27.

As described above, in the automatic analyzer 1 of the first embodiment, the control unit 16 controls the position of the photometry unit 10 according to the position at which the liquid is held in the reaction vessel 7, so that the photometric position may be controlled in accordance with the position of the liquid held in the reaction vessel 7, and this allows the photometry of the liquid held in the reaction vessel 7 even when the liquid is not introduced to the bottom portion of the reaction vessel as in the conventional analyzer.

Next, a second embodiment of the analyzer of the present invention will be described in detail with reference to the drawings. In the automatic analyzer of the first embodiment, the control unit 16 has decided the vertical position and the photometric position of the photometry unit 10 based on the dispensing amounts of the specimen and the reagent input from the specimen dispensing mechanism 5 and the reagent dispensing mechanism 12, respectively. On the other hand, in the automatic analyzer of the second embodiment, the position of the liquid held in the vessel is detected by the surface acoustic wave device, which is the stirring means.

Figure 28:
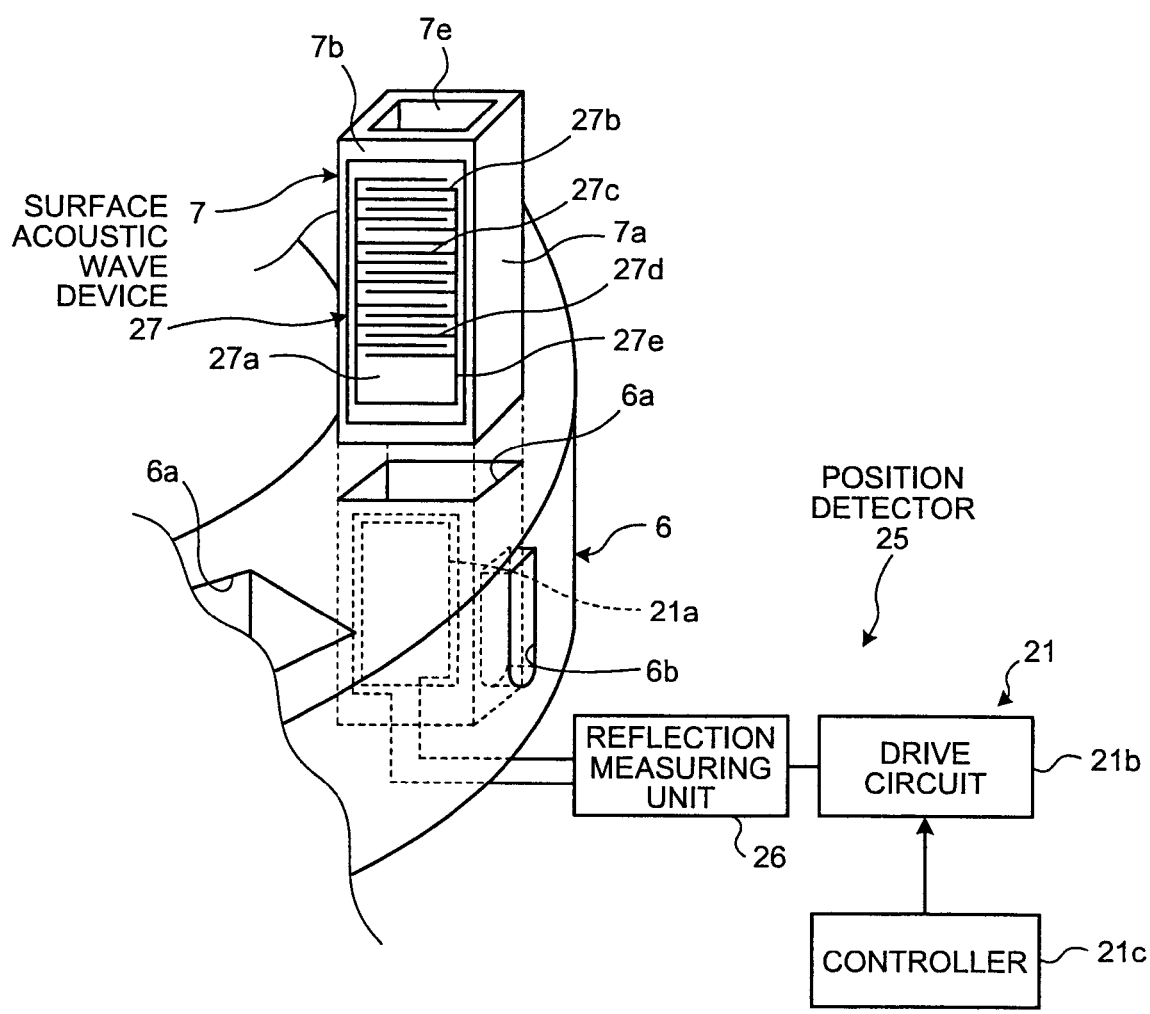
FIG. 28 is a perspective view showing the automatic analyzer of a second embodiment together with a schematic configuration diagram of the reaction vessel, a part of the reaction wheel and the stirrer.
Figure 29:
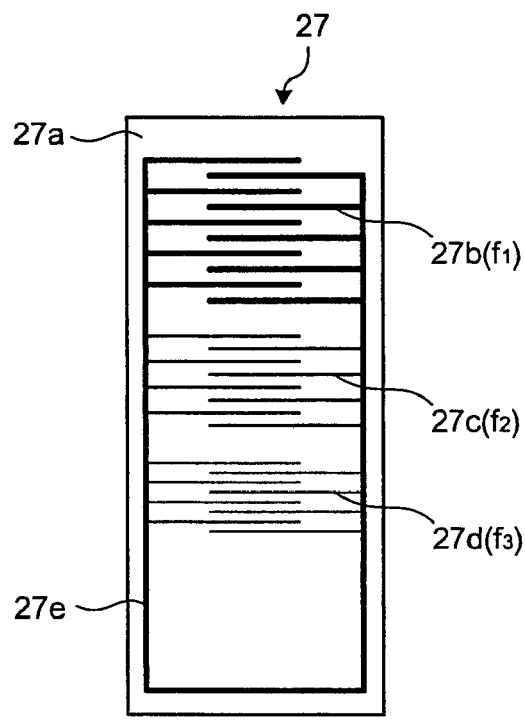
FIG. 29 is a front view showing the surface acoustic wave device used in the reaction vessel shown in FIG. 28 and used in position detection of the liquid held in the reaction vessel.

FIG. 28 is a perspective view showing the automatic analyzer of the second embodiment together with a schematic configuration diagram of the reaction vessel, a part of the reaction wheel, and the stirrer. FIG. 29 is a front view showing the surface acoustic wave device used in the reaction vessel shown in FIG. 28 and used for detecting the position of the liquid held in the reaction vessel. Herein, a basic configuration of the automatic analyzer of the second embodiment is the same as that of the automatic analyzer of the first embodiment. Therefore, in the automatic analyzer of each embodiment to be described later, the same reference numeral is used for the same component as the automatic analyzer of the first embodiment.

The automatic analyzer of the second embodiment is provided with a position detector 25, which is obtained by serially connecting a reflection measuring unit 26 between the drive circuit 21b and the RF transmission antenna 21a, as shown in FIG. 28. The position detector 25 has the reflection measuring unit 26, a surface acoustic wave device 27 and the controller 21c, and doubles as the stirring means for stirring the liquid held in the reaction vessel.

The reflection measuring unit 26 is a measuring section for measuring electrical characteristics of transducers 27b to 27d, which are the sound generating elements of the surface acoustic wave device 27. The reflection measuring unit 26 is for measuring reflectivity of electrical energy (electrical power) reflected by and returned from the transducers 27b to 27d with respect to the electrical power generated in the drive circuit 21b and output from the RF transmission antenna 21a to the surface acoustic wave device 27, and a standing wave ratio (SWR) calculator is used, for example. The reflection measuring unit 26 outputs the measured reflectivity of electrical power to the controller 21c as a reflection signal. Herein, the reflection measuring unit 26 may measure at least one of values regarding impedance, voltage and current in addition to the reflectivity of the electrical power from the transducers 27b to 27d, which are the sound generating elements, as long as this may measure the electrical characteristics of the transducers 27b to 27d.

The surface acoustic wave device 27 is sound wave generating means having a plurality of sound generating elements, and as shown in FIG. 29, the transducers 27b to 27d, which are the sound generating elements formed of the interdigital transducers (IDTs), are formed on the piezoelectric substrate 27a formed of the same material as that of the piezoelectric substrate 22a, and the transducers 27b to 27d are parallelly connected by an antenna 27e. At this time, the surface acoustic wave device 27 sets the center frequencies of the transducers 27b to 27d to f1 to f3 (f1<f2<f3) and is attached to the side wall 7b of the reaction vessel 7 through the acoustic matching layer.

The controller 21c is a determination control unit for determining presence or absence of the liquid at the position of each of the transducers 27b to 27d, which are the sound generating elements, by utilizing the difference in the electrical characteristics measured at the reflection measuring unit 26. The controller 21c determines presence or absence of the liquid held in the reaction vessel based on the reflection signal input from the reflection measuring unit 26, detects the position of the liquid, and decides the transducer to be used to stir the liquid out of the transducers 27b to 27c. At this time, the controller 21c, which has decided the transducer to be used, outputs the control signal to the drive circuit 21b and changes the oscillation frequency so as to drive the decided transducer with the center frequency.

The position detector 25 thus configured detects presence or absence and the position of the liquid held in the reaction vessel 7 by a position detecting method to be described later. That is, the position detecting method by the position detector 25 includes a process to change with time the frequency of the drive signal of the surface acoustic wave device 27 output by the drive circuit 21b to the RF transmission antenna 21a and to individually generate the sound wave from the transducers 27b to 27d, a process to measure the reflectivities of the drive signal from each of the transducers 27b to 27d based on the individually generated sound waves, and a process to determine presence or absence of the liquid at the position of each of the transducers 27b to 27d based on the difference in the measured reflectivities. The position detector 25 may detect presence or absence and the position of the liquid held in the reaction vessel 7 by this position detecting method.

Figure 30:
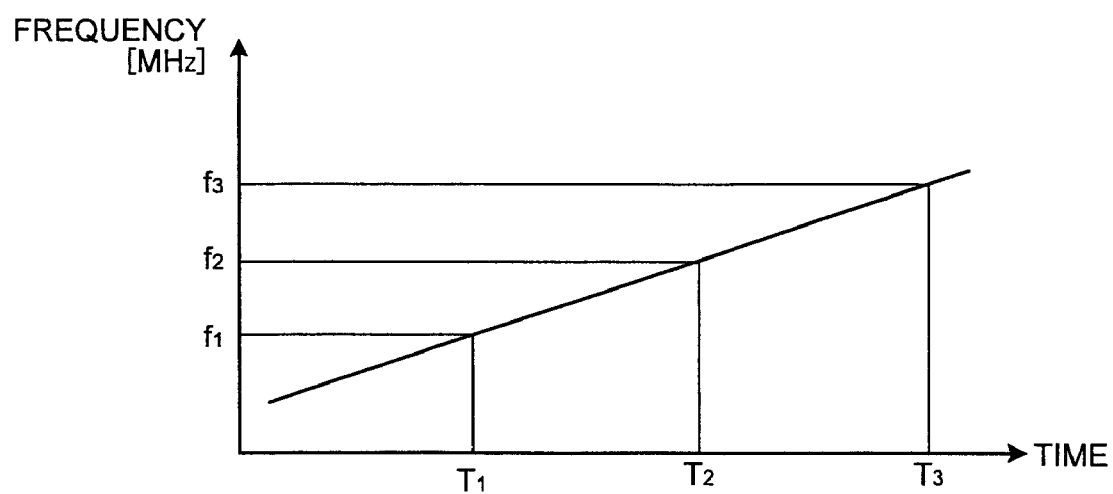
FIG. 30 is a time variation diagram of frequency showing an example of drive with time of the surface acoustic wave device shown in FIG. 29.
Figure 31:
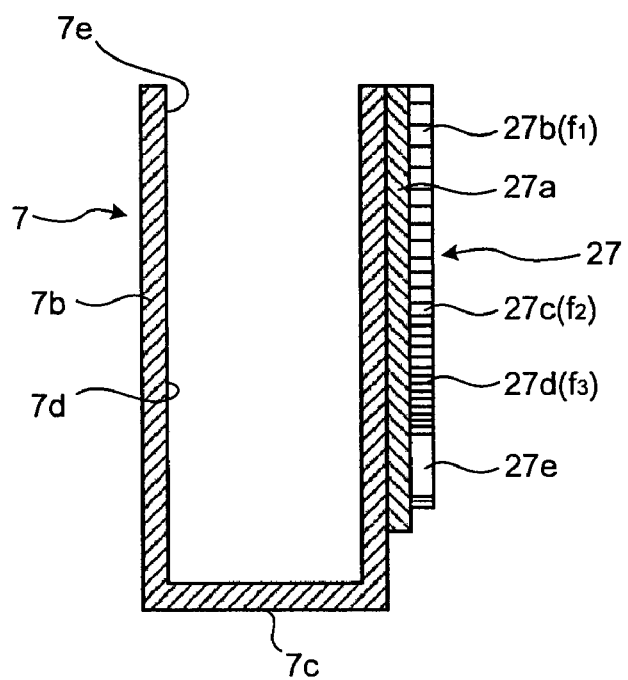
FIG. 31 is a cross-sectional view showing a case in which the liquid holding section of the reaction vessel to which the surface acoustic wave device shown in FIG. 29 is attached is empty.
Figure 32:
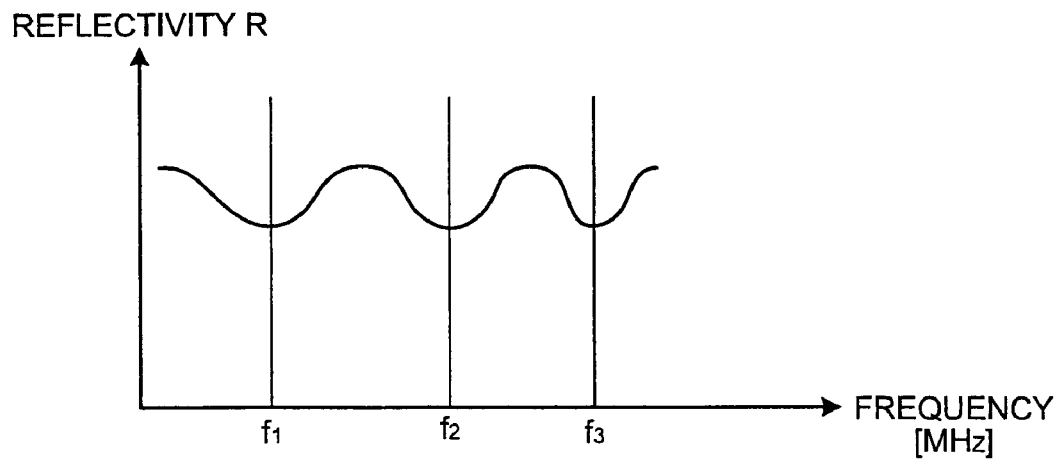
FIG. 32 is a frequency characteristic diagram regarding reflectivity of a drive signal in a case in which the surface acoustic wave device shown in FIG. 31 is driven.

Herein, the position detector 25 linearly changes with time the frequency of the drive signal of the surface acoustic wave device 27, output by the drive circuit 21b to the RF transmission antenna 21a, for example, as shown in FIG. 30, when executing the position detecting method. In such a case, in the reaction vessel 7, the liquid holding section 7d is in an empty state, as shown in FIG. 31, if the specimen and reagent are not dispensed. At this time, in the position detector 25, as shown in FIG. 30, when the frequency of the drive signal is changed, the frequency becomes f1, f2 and f3 at times T1, T2 and T3, and the transducers 27b to 27d are driven in the order of transducers 27b, 27c and 27d. However, in the reaction vessel 7, since the liquid holding section 7d is empty, the generated sound wave does not leak into the liquid and a part of electrical power output from the drive circuit 21b is sequentially reflected from the transducers 27b to 27d. Therefore, the reflection measuring unit 26 outputs the reflection signals from the transducers 27b to 27d in which the reflectivities of the drive signals of the frequencies f1, f2 and f3 become the smallest at the times T1, T2 and T3, as shown in FIG. 32, to the controller 21c.

Figure 33:
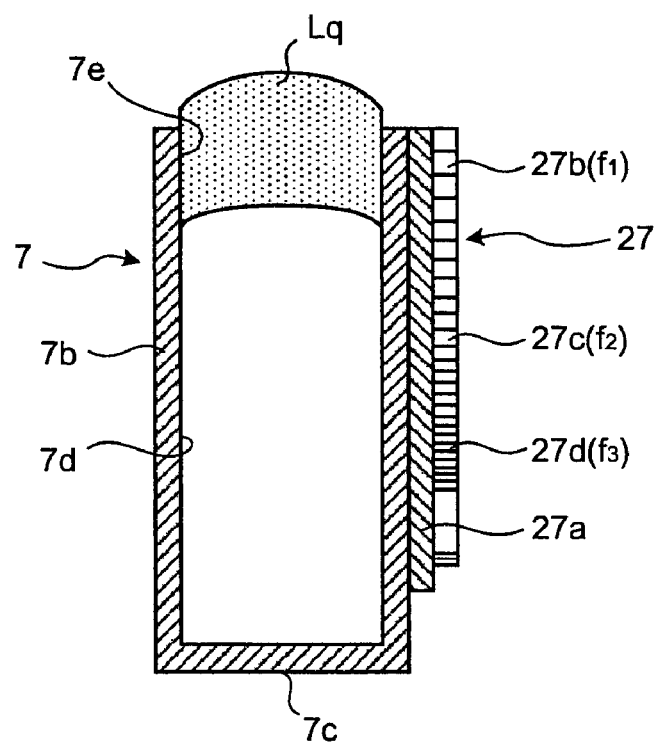
FIG. 33 is a cross-sectional view showing a case in which the liquid is held in the vicinity of the opening on an upper portion of the liquid holding section of the reaction vessel shown in FIG. 29.
Figure 34:
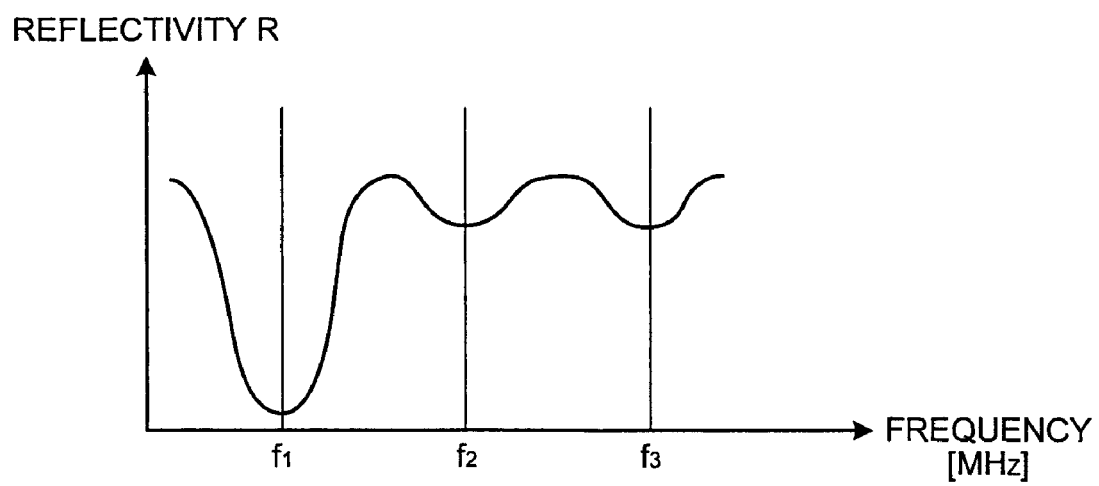
FIG. 34 is a frequency characteristic diagram regarding reflectivity of a drive signal in a case in which the surface acoustic wave device shown in FIG. 33 is driven.

On the other hand, in a case in which the dispensing amounts of the specimen and the reagent are small, in the reaction vessel 7, the liquid Lq is held in the vicinity of the opening 7e by the surface tension, as shown in FIG. 33. At this time, in the position detector 25, as shown in FIG. 30, when the frequency of the drive signal is changed, since the transducer 27b is the closest to the liquid Lq, the amount of the sound wave generated by the transducer 27b leaking into the liquid is the largest, and the amount of the sound wave generated by the transducers 27c and 27d leaking into the liquid is smaller. Therefore, the reflection measuring unit 26 outputs the reflection signal (frequency f1) in which the reflectivity from the transducer 27b becomes significantly smaller than the reflectivities from the transducers 27c and 27d, as shown in FIG. 34, to the controller 21c. At this time, the reflectivities of the drive signals (frequencies f2 and f3) reflected from the transducers 27c and 27d are larger than the reflectivity of the drive signal of the frequency f1 and substantially equal to the reflectivity of the drive signals (frequencies f2 and f3) of the transducers 27c and 27d in FIG. 32 because the liquid does not exist in the liquid holding section 7d corresponding to the transducers 27c an 27d and the sound wave does not leak into the liquid.

Figure 35:
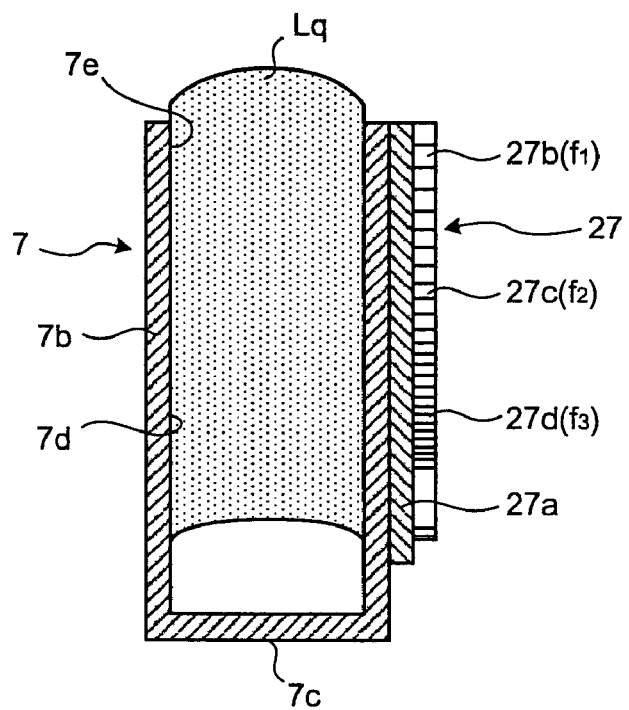
FIG. 35 is a cross-sectional view showing a case in which the liquid is held from the vicinity of the opening of the reaction vessel shown in FIG. 29 to near the lower portion of the liquid holding section.
Figure 36:
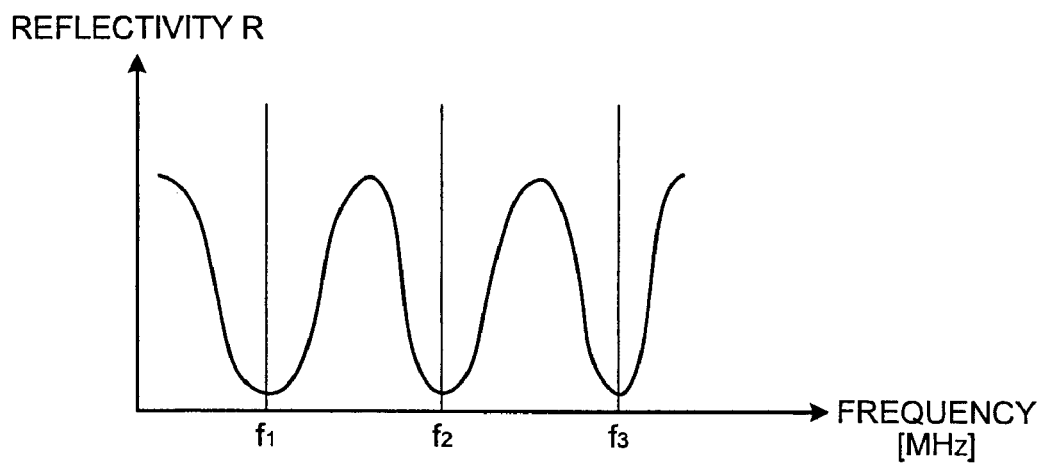
FIG. 36 is a frequency characteristic diagram regarding reflectivity of a drive signal in a case in which the surface acoustic wave device shown in FIG. 35 is driven.

On the other hand, if the specimen and the reagent are dispensed in large volume, in the reaction vessel 7, the liquid Lq is held from the vicinity of the opening 7e to near the lower portion of the liquid holding section 7d, as shown in FIG. 35. In such a state, the positions of the transducers 27b to 27d and the position of the liquid Lq are close to each other. Therefore, in the position detector 25, as shown in FIG. 30, when the frequency of the drive signal is changed, the sound wave generated from each of the transducers 27b to 27d leaks into the liquid and the reflectivities of the drive signals from the transducers 27b to 27d become smaller. As a result, the reflection measuring unit 26 outputs the reflection signal in which the reflectivities of the drive signals (frequencies f2 and f3) of the transducers 27c and 27d also become the smallest in addition to the reflectivity of the drive signal (frequency f1) of the transducer 27b, as shown in FIG. 36 to the controller 21c.

Figure 37:
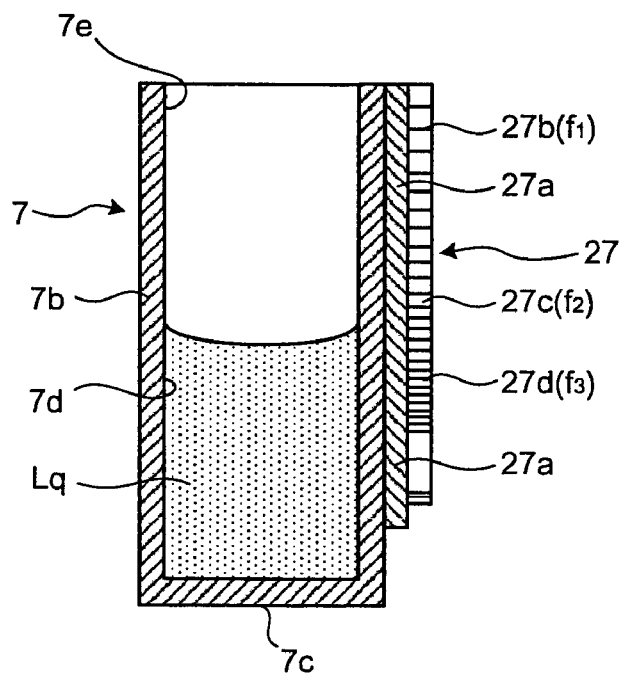
FIG. 37 is a cross-sectional view showing a case in which the liquid intrudes into the bottom portion of the reaction vessel shown in FIG. 29.
Figure 38:
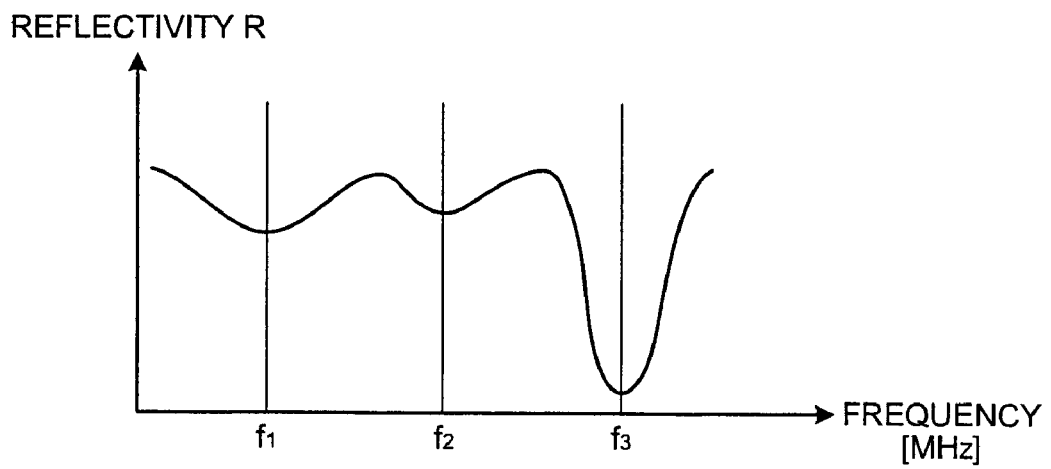
FIG. 38 is a frequency characteristic diagram regarding reflectivity of a drive signal in a case in which the surface acoustic wave device shown in FIG. 37 is driven.

Further, there is a case in which the liquid Lq intrudes into the bottom portion of the reaction vessel 7, as shown in FIG. 37, due to the extremely small surface tension or the large density $\rho$, for example, even though the dispensing amounts of the specimen and the reagent are moderate. In such a case, the position of the transducer 27d and the position of the liquid Lq are close to each other. Therefore, in the position detector 25, as shown in FIG. 30, when the frequency of the drive signal is changed, the sound wave generated from the transducer 27d leaks into the liquid and leaking amounts of the sound waves generated by the transducers 27b and 27c become smaller. As a result, the reflection measuring unit 26 outputs the reflection signal in which the reflectivity of the drive signal (frequency f3) of the transducer 27d is significantly smaller than the reflectivities of the drive signals (frequencies f1 and f2) of the transducers 27b and 27c, as shown in FIG. 38, to the controller 21c.

From the above description, the position detector 25 may detect the position of the liquid held in the reaction vessel 7, in addition to presence or absence of dispensing of the liquid to the reaction vessel 7 (presence or absence of the liquid), by determining a magnitude of the reflectivities of the drive signal output from the reflectivity measure 26 to the controller 21c, at the controller 21c.

Therefore, the automatic analyzer of the second embodiment may optimally stir the liquid held in the reaction vessel 7 by allowing the control unit 16 to select the transducers 27b to 27d to be driven according to the position of the liquid in the reaction vessel 7 detected by the controller 21c of the position detector 25. At this time, the automatic analyzer of the second embodiment adjusts the vertical position of the photometry unit 10 by means of the driver Dr by the control unit 16 according to the position of the liquid detected by the position detector 25, in addition to the photometric position control performed by the automatic analyzer of the first embodiment, to control the photometric position in accordance with the position of the liquid, thereby performing the photometry.

Accordingly, in the automatic analyzer of the second embodiment, the control unit 16 controls the position of the photometry unit 10 according to the position at which the liquid is held in the reaction vessel 7, so that it is possible to control the photometric position in accordance with the position of the liquid held in the reaction vessel 7, and this allows for the photometry of the liquid held in the reaction vessel 7 even when the liquid is not introduced to the bottom portion of the reaction vessel as in the conventional analyzer.

Especially, the automatic analyzer of the second embodiment allows for the photometry by the photometry unit 10 at the position of the liquid held in the reaction vessel 7, by allowing the position detector 25 to detect the position at which the liquid is held in the reaction vessel 7. In addition, the position detector 25 and the position detecting method of the second embodiment may detect the position of the liquid held in the reaction vessel 7 with a simple configuration. Also, the automatic analyzer of the second embodiment allows for the photometry at the position of the liquid held in the reaction vessel 7. Further, the position detector 25 and the position detecting method of the second embodiment may detect the position of the liquid from outside the reaction vessel 7 without contacting the liquid in the reaction vessel 7, so that this may prevent another substance from being mixed into the reaction vessel 7 when used in the automatic analyzer.

Herein, although the automatic analyzer of the second embodiment linearly changes with time the frequency of the drive signal of the surface acoustic wave device 27 used in the position detector 25, as shown in FIG. 30, it is possible to gradually change the frequency of the drive signal as the frequency f1 until the time T1, the frequency f2 between the times T1 and T2, and the frequency f3 after the time T2.

Meanwhile, in the position detector 25, although three transducers 27b to 27d are used as the sound generating elements of the surface acoustic wave device 27, the number of the sound generating elements is not limited to three and more accurate position detection becomes possible by increasing the number thereof to be set according to the size of the reaction vessel.

Figure 39:
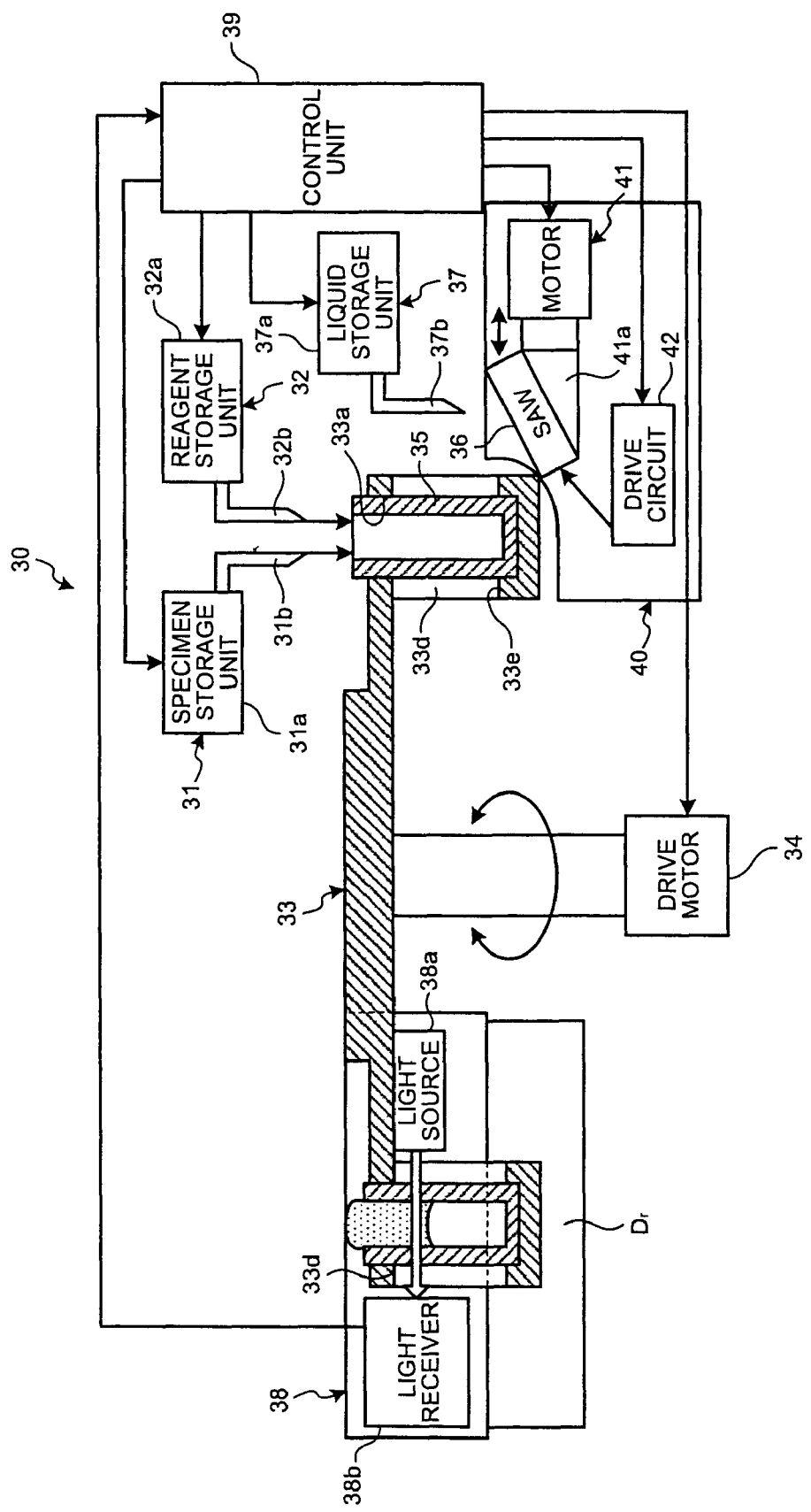
FIG. 39 is a block diagram showing a configuration of the automatic analyzer of a third embodiment by showing a cross-section of the reaction vessel and the reaction table.
Figure 40:
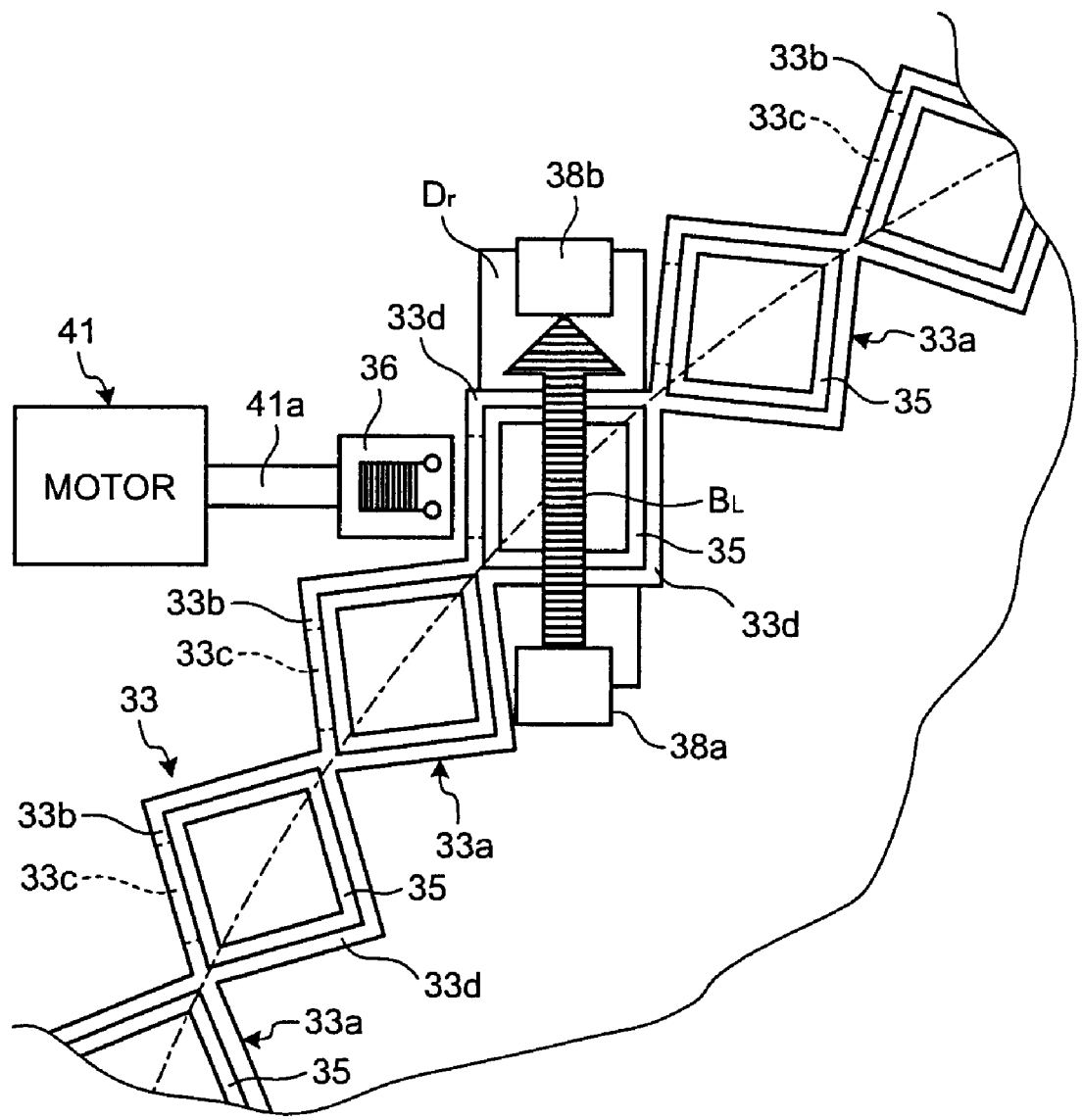
FIG. 40 is a plan view showing a part of the reaction table used in the automatic analyzer in FIG. 39 together with the surface acoustic wave device and the driver thereof.

Next, a third embodiment of the analyzer of the present invention will be described in detail with reference to the drawings. Although the surface acoustic wave device has been attached to the reaction vessel in the automatic analyzers of the first and second embodiments, the automatic analyzer of the third embodiment is configured such that the surface acoustic wave device located in the vicinity of the reaction vessel is disjunctive. FIG. 39 is a block diagram showing the configuration of the automatic analyzer of the third embodiment by showing the cross section of the reaction vessel and the reaction table. FIG. 40 is a plan view of a part of the reaction table used in the automatic analyzer in FIG. 39 together with the surface acoustic wave device and a driver thereof.

An automatic analyzer 30 is provided with a specimen dispensing section 31, a reagent dispensing section 32, a reaction table 33, a surface acoustic wave device 36, a photometry unit 38, a control unit 39 and a stirring unit 40, as shown in FIG. 39.

The specimen dispensing section 31 dispenses the specimen accommodated in a specimen storage unit 31a to a reaction vessel 35 by a specimen nozzle 31b, as shown in FIG. 39. The reagent dispensing section 32 dispenses the reagent accommodated in a reagent storage unit 32a to the reaction vessel 35 by a reagent nozzle 32b. The specimen dispensing section 31 and the reagent dispensing section 32 are separately driven by drive means and move above an outer circumference of the reaction table 33 in a two-dimensional direction along the surface thereof. The specimen dispensing section 31 and the reagent dispensing section 32 output the dispensing amounts of the specimen and the reagent dispensed to the reaction vessel 35 to the control unit 39.

The reaction table 33 is rotated by a drive motor 34, and a plurality of concave-shaped holders 33a arranged along the circumferential direction are provided on the outer circumference thereof, as shown in FIGS. 39 and 40. The reaction vessel 35 is detachably accommodated in the holder 33a. Also, in the reaction table 33, an abutting window 33c formed of an opening is formed in a central portion of an outer surface of a side wall 33b and a photometric window 33e extending in the vertical direction is formed on a side wall 33d adjacent to the side wall 33b. At this time, the holder 33a is formed such that the side wall 33b on which the abutting window 33c is formed and the side wall 33b facing the same are inclined at 45 degrees relative to the radial direction, and the two side walls 33d forming the photometric window 33e are formed so as to be parallel to each other.

Figure 42:
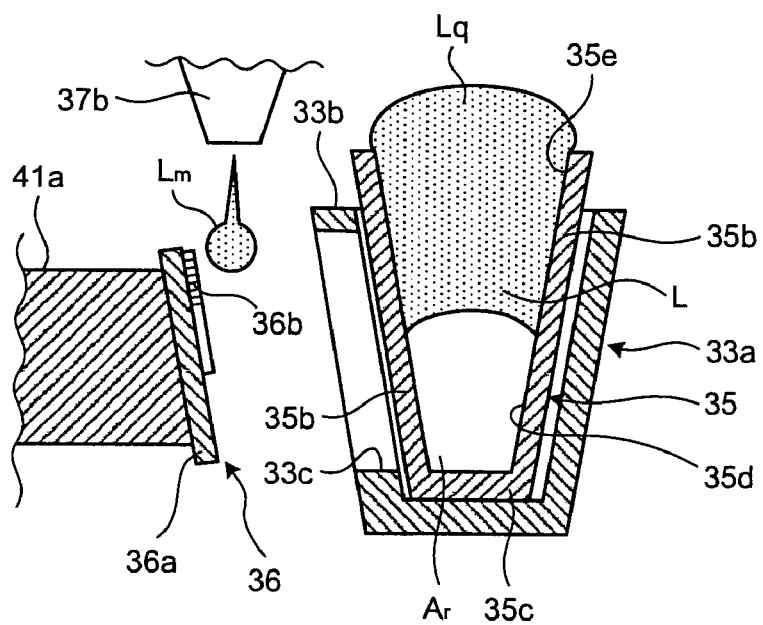
FIG. 42 is a cross-sectional view showing an arrangement of a holder, the reaction vessel and the surface acoustic wave device on the reaction table forming the automatic analyzer in FIG. 39 and acoustic matching liquid dropped on the surface acoustic wave device.
Figure 43:
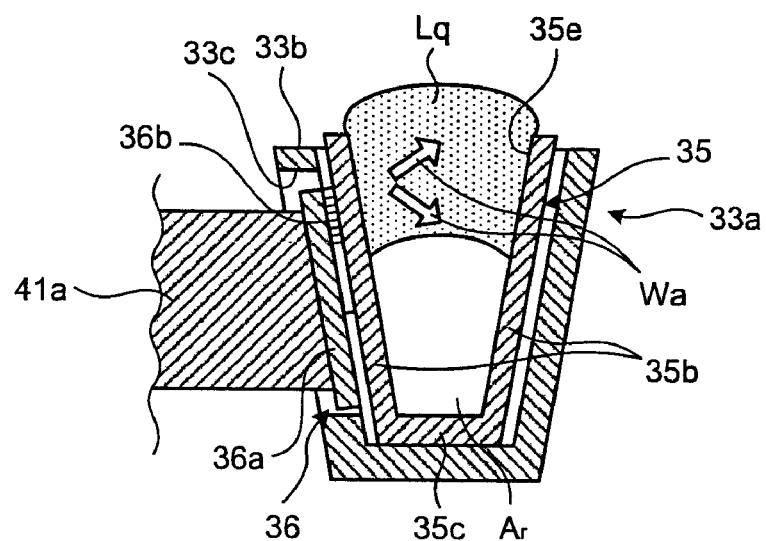
FIG. 43 is a cross-sectional view corresponding to FIG. 42 showing a state in which the surface acoustic wave device abuts a side wall of the reaction vessel though an abutting window formed in the holder.
Figure 44:
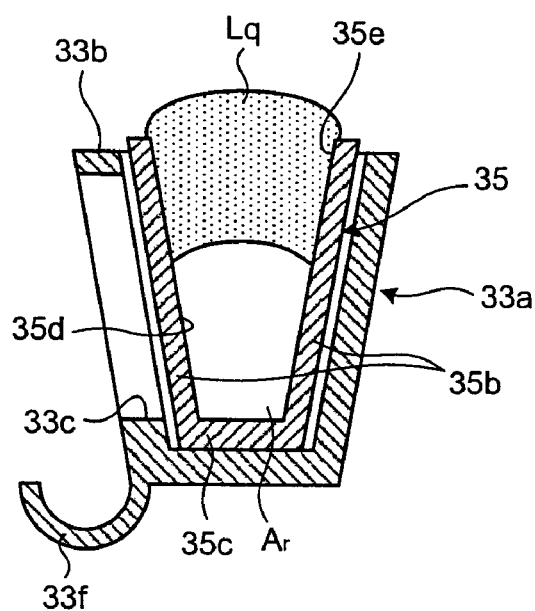
FIG. 44 is a cross-sectional view corresponding to FIG. 42 showing a modified example of the holder.

Herein, although a plurality of holders 33a are provided on the outer circumference of the reaction table 33 along the circumferential direction thereof, as shown in FIG. 40, in FIGS. 42 to 44, for convenience of clearly showing the configuration, only one holder 33a is shown. Also, as shown in FIG. 39, the surface acoustic wave device 36 and the photometry unit 38 are arranged on opposed positions in a diameter direction of the reaction table 33; however, in FIG. 40, the surface acoustic wave device 36 is shown to be arranged in the vicinity of the photometry unit 38 to clearly and simply show the arrangement of the surface acoustic wave device 36 and the photometry unit 38.

Figure 17:
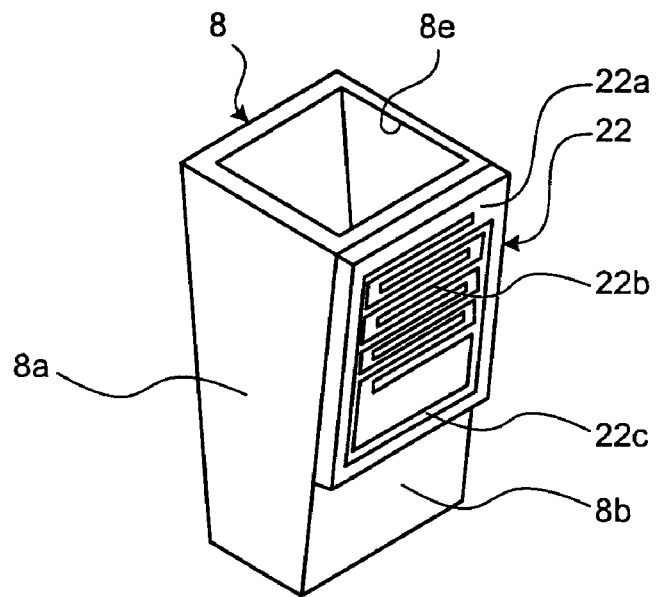
FIG. 17 is a perspective view showing a first modified example of the reaction vessel.

The reaction vessel 8 in a rectangular tubular shape shown in FIGS. 17 and 18 described in the first embodiment for holding the small amount of liquid of a few nanoliters (nL) to several tens of microliters (μL) in the liquid holding section 35d is used as the reaction vessel 35; however, the surface acoustic wave device 36 is not attached to the side wall 35b but is arranged in the vicinity thereof.

Figure 41:
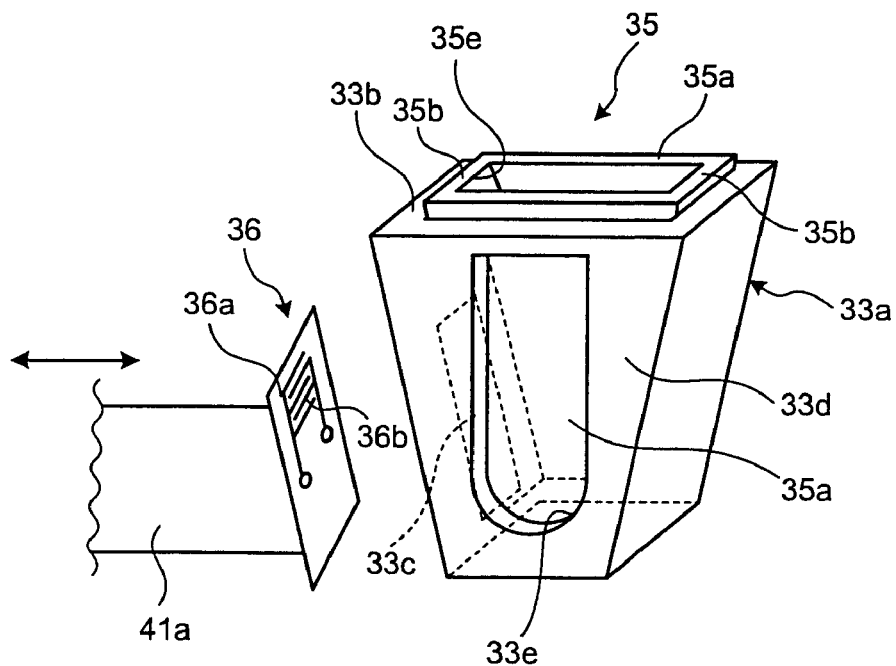
FIG. 41 is a perspective view showing an arrangement of a holder, the reaction vessel and the surface acoustic wave device on the reaction table forming the automatic analyzer in FIG. 39.

The surface acoustic wave device 36 is the stirring means for stirring the liquid held in the reaction vessel 35 by the sound wave (surface acoustic wave: SAW), and as shown in FIGS. 40 to 42, a transducer 36b, which is the sound generating element formed of the interdigital transducer (IDT), is formed on a piezoelectric substrate 36a, and is driven by the electrical power supplied from a drive circuit 42 (see FIG. 39) of the stirring unit 40. Also, the surface acoustic wave device 36 is attached to a tip end of an arm 41a driven in a direction indicated by an arrow by a motor 41, as shown in FIG. 39, and is disjunctive to a side wall 35b of the reaction vessel 35 through the abutting window 33c formed on the side wall 33b. At this time, the surface acoustic wave device 36 is arranged at an inclination so as to face the side wall 35b of the reaction vessel 35 held by the holder 33a, and acoustic matching liquid held in a liquid storage unit 37a of a liquid dispensing section 37 arranged in the upper vicinity thereof is dropped from a nozzle 37b.

As shown in FIG. 39, the photometry unit 38 has a light source 38a for emitting a bundle of light (see FIG. 40) of analytical light (340 to 800 nm) for analyzing the liquid held in the reaction vessel 35 and a light receiver 38b for dispersing and receiving the bundle of light penetrating the liquid, arranged so as to face each other in a radial direction of the reaction table 33 with the holder 33a interposed therebetween. In the photometry unit 38, a vertical position (photometric position) of the light source 38a and the light receiver 38b is controlled by the driver Dr provided in the lower portion and controlled by the control unit 39. Herein, the reaction vessel 35 of which photometry at the photometry unit 38 is finished is transferred to the cleaner and is cleaned, and after that, used again for analyzing the new specimen.

The control unit 39 is connected to the specimen dispensing section 31, the reagent dispensing section 32, the drive motor 34, the liquid dispensing section 37, the photometry unit 38 and the stirring unit 40, as shown in FIG. 39, and the microcomputer or the like incorporating a memory and a timer for storing the analytical result is used, for example. The control unit 39 controls operation of each section of the automatic analyzer 30 to analyze constituent concentration or the like of the specimen based on information of the transmitted light output from the light receiver 38b. Also, the control unit 39 is provided with the input unit such as the keyboard and the mouse for performing operation of inputting the inspection item or the like and the display panel for displaying the analytical content, the alert or the like.

Herein, the control unit 39 controls characteristics (frequency, intensity, phase, characteristics of wave), waveforms (sine wave, triangle wave, rectangular wave, burst wave, or the like) or modulations (amplitude modulation, frequency modulation) or the like of the sound wave generated by the surface acoustic wave device 36, when controlling the stirring unit 40. Also, the control unit 39 may switch the frequency of the oscillation signal oscillated by the drive circuit 42 according to the incorporated timer.

The control unit 39 obtains in advance the table and the function for deciding the vertical position, that is, the photometric position, of the photometry unit 38 based on the dispensing amounts of the specimen and the reagent input from the specimen dispensing section 31 and the reagent dispensing section 32, respectively, and controls the position of the driver Dr based on the table and the function, thereby controlling the photometric position of the photometry unit 38. Herein, in the control unit 39, when the measurement item of the specimen and the position information of the reaction vessel 35 are input from the input unit, signals corresponding to the measurement item and the position information of the reaction vessel 35, which have been input, are input from the input unit. The control unit 39 allows the specimen dispensing section 31 and the reagent dispensing section 32 to dispense the specimen and the reagent to the specified reaction vessel 35 in a predetermined amount, based on these signals.

At this time, the specimen dispensing section 31 and the reagent dispensing section 32 output the dispensing amount signals regarding the dispensing amounts of the specimen and the reagent dispensed to the reaction vessel 35 to the control unit 39, as described above. The control unit 39 outputs the dispensing amount signal to the stirring unit 40 and, reads the photometric position measured in advance and stored regarding the reaction vessel 35 based on the dispensing amount signals thus input, and controls the photometric position of the photometry unit 38 by means of the driver Dr.

The stirring unit 40 is the section for stirring the liquid held in the reaction vessel 35 by driving the surface acoustic wave device 36 under the control of the control unit 39, and has the motor 41 and the drive circuit 42 as shown in FIG. 39. The motor 41 drives the arm 41a, moves the surface acoustic wave device 36 in a direction indicated by an arrow shown in FIG. 39, and allows the same to abut the side wall 35b of the reaction vessel 35 through the abutting window 33c of the holder 33a at the time of stirring (see FIG. 43), under the control of the control unit 39.

The drive circuit 42 has the oscillation circuit capable of programmably changing the oscillation frequency based on the control signal from the control unit 39, amplifies the oscillation signal of high frequency of about several tens of MHz to several hundreds of MHz and outputs the same to the surface acoustic wave device 36 as the drive signal, as well as gradually switches the drive frequency of the drive signal based on the control signal from the control unit 39.

The automatic analyzer 30 configured in this manner analyzes the specimen dispensed to the reaction vessel 35 by the photometric method to be described below including a process to control the photometric position at which the photometry of the liquid is performed according to the holding position at which the liquid is held in the reaction vessel 35, and a process to perform the photometry of the liquid at the controlled photometric position.

First, the automatic analyzer 30 rotates the reaction table 33 and stops the holder 33a holding the reaction vessel 35 to be dispensed at a reagent dispensing position under the control of the control unit 39. Next, in the automatic analyzer 30, the reagent dispensing section 32 dispenses a first reagent from above the reaction vessel 35 to the opening 35a, by the reagent nozzle 32b under the control of the control unit 39. At this time, since the capacity of the reaction vessel 35 is as extremely small as a few nanoliters (nL) to several tens of microliters (μL), the first reagent is held in the vicinity of the opening 35e through air at the lower portion according to at least one of the kind or the amount thereof and the form or the material of the reaction vessel 35. The control unit 39 controls the vertical position (photometric position) of the photometry unit 38 by the driver Dr based on the dispensing amount of the first reagent output by the reagent dispensing section 32.

Next, the automatic analyzer 30 rotates the reaction table 33 to move the reaction vessel 35 to which the first reagent has been dispensed to the photometry unit 38 under the control of the control unit 39. Thereby, in the reaction vessel 35, the analytical light emitted from the light source 38a is applied from the photometric window 33e of the holder 33a and the photometry of the bundle of light penetrated the first reagent is performed by the light receiver 38b at the appropriate photometric position in the vicinity of the opening 35e. The light receiver 38b outputs light information regarding the received bundle of light to the control unit 39. The control unit 39 calculates light absorbance of the first reagent based on the light information and stores the same.

After blank photometry regarding the first reagent is finished in this manner, the automatic analyzer 30 drives the drive motor 34 to rotate the reaction table 33 and moves the reaction vessel 35 to which the first reagent has been dispensed to the specimen dispensing section 31 under the control of the control unit 39. Next, the automatic analyzer 30 dispenses the specimen from the specimen nozzle 31b on the first reagent held in the vicinity of the opening 35e of the reaction vessel 35 under the control of the control unit 39. At this time, the control unit 39 controls the vertical position (photometric position) of the photometry unit 38 by the driver Dr based on the dispensing amount of the specimen output from the specimen dispensing section 31.

Next, the automatic analyzer 30 drives the transducer 36b by the drive circuit 42 and stirs the first reagent and the specimen by the generated sound wave (surface acoustic wave) to react them under the control of the control unit 39. Thereafter, the automatic analyzer 30 drives the drive motor 34 to rotate the reaction table 33 and moves the reaction vessel 35 to the photometry unit 38, under the control of the control unit 39. Thereby, in the reaction vessel 35, the photometry of reaction liquid obtained by reacting the first reagent and the specimen is performed at the appropriate photometric position in the vicinity of the opening 35e. The control unit 39 calculates the light absorbance of the reaction liquid obtained by reacting the first reagent and the specimen based on the light information obtained by the light receiver 38b and stores the same.

Next, the automatic analyzer 30 drives the drive motor 34 to rotate the reaction table 33 and moves the reaction vessel 35 holding the reaction liquid of the first reagent and the specimen to the reagent dispensing section 32, under the control of the control unit 39. After that, the automatic analyzer 30 dispenses a second reagent from the reagent nozzle 32b on the reaction liquid held in the vicinity of the opening 35e of the reaction vessel 35 under the control of the control unit 39. At this time, the control unit 39 controls the photometric position of the photometry unit 38 based on the dispensing amount of the second reagent output by the reagent dispensing section 32. Next, the automatic analyzer 30 drives the motor 41 to run out the arm 41a and allows the same to abut the side wall 35b of the reaction vessel 35, and drives the transducer 36b by the drive circuit 42 to stir the reaction liquid of the first reagent and the specimen and the second reagent by the generated sound wave (surface acoustic wave) to react them under the control of the control unit 39.

After that, the automatic analyzer 30 drives the motor 41 to draw in the arm 41a, which has been run out, and drives the drive motor 34 to rotate the reaction table 33 to move the reaction vessel 35 to the photometry unit 38, under the control of the control unit 39. Thereby, in the reaction vessel 35, the photometry of the reaction liquid obtained by reacting the reaction liquid of the first reagent and the specimen with the second reagent is performed at the appropriate photometric position in the vicinity of the opening 35e of the reaction vessel 35. The control unit 39 calculates the light absorbance of the reaction liquid obtained by reacting the reaction liquid of the first reagent and the specimen with the second reagent based on the light information obtained by the light receiver 38b and calculates the constituent concentration or the like of the specimen based on the light absorbance of the first reagent and the light absorbance of the mixed liquid of the first reagent and the specimen measured in advance. Then, the reaction vessel 35 in which photometry at the photometry unit 38 is finished is transferred to the cleaner and the reaction liquid is discharged and is cleaned, and thereafter, used again for analyzing the new specimen.

Herein, the automatic analyzer 30 drops acoustic matching liquid Lm on the surface of the surface acoustic wave device 36 by the nozzle 37b of the liquid dispensing section 37 as shown in FIG. 42 under the control of the control unit 39 upon stirring of the liquid by the surface acoustic wave device 36. At this time, the reaction vessel 35 holding the liquid Lq is inserted to the holder 33a in the vicinity of the opening 35e. Next, the automatic analyzer 30 runs out the arm 41a by the motor 41 and allows the surface acoustic wave device 36 to abut the side wall 35b of the reaction vessel 35 through the abutting window 33c under the control of the control unit 39, as shown in FIG. 43. Thereby, a thin film of the acoustic matching liquid Lm is arranged between the surface acoustic wave device 36 and the side wall 35b, so that the sound wave (surface acoustic wave) generated by the surface acoustic wave device 36 leaks into the liquid Lq held in the reaction vessel 35 through the side wall 35b and the liquid Lq is stirred by the leaked sound wave Wa.

In this manner, in the automatic analyzer 30 of the third embodiment, the control unit 39 controls the position of the photometry unit 38 according to the position at which the liquid of the reaction vessel 35 is held, it is possible to control the photometric position in accordance with the position of the liquid held in the reaction vessel 35, and this allows for the photometry of the liquid held in the reaction vessel 35 even though the liquid is not introduced to the bottom portion of the reaction vessel 35 as in the conventional analyzer. At this time, the automatic analyzer 30 performs the photometry of the liquid in the vicinity of the opening 35e in a state in which the liquid is held in the vicinity of the opening 35e of the reaction vessel 35. Therefore, the automatic analyzer 30 does not require means for sending the liquid to the inside the reaction vessel 35.

However, the position at which the reaction vessel 35 holds the liquid including the reagent R and the specimen S varies according to at least one of the kind or the amount of the liquid and the form or the material of the reaction vessel 35. Therefore, in such a case, the control unit 39 reads the photometric position stored in advance based on the dispensing amount signals regarding the dispensing amounts of the specimen and the reagent input from the specimen dispensing section 31 and the reagent dispensing section 32, respectively, and controls the photometric position by the photometry unit 38 by means of the driver Dr.

Herein, the acoustic matching liquid Lm is easy to flow when viscosity thereof is low. Therefore, in the holder 33a, it is preferable to provide a skirt portion 33f on a lower portion of the abutting window 33c side for receiving the acoustic matching liquid Lm dropped on the surface acoustic wave device 36, as shown in FIG. 44.

Figure 45:
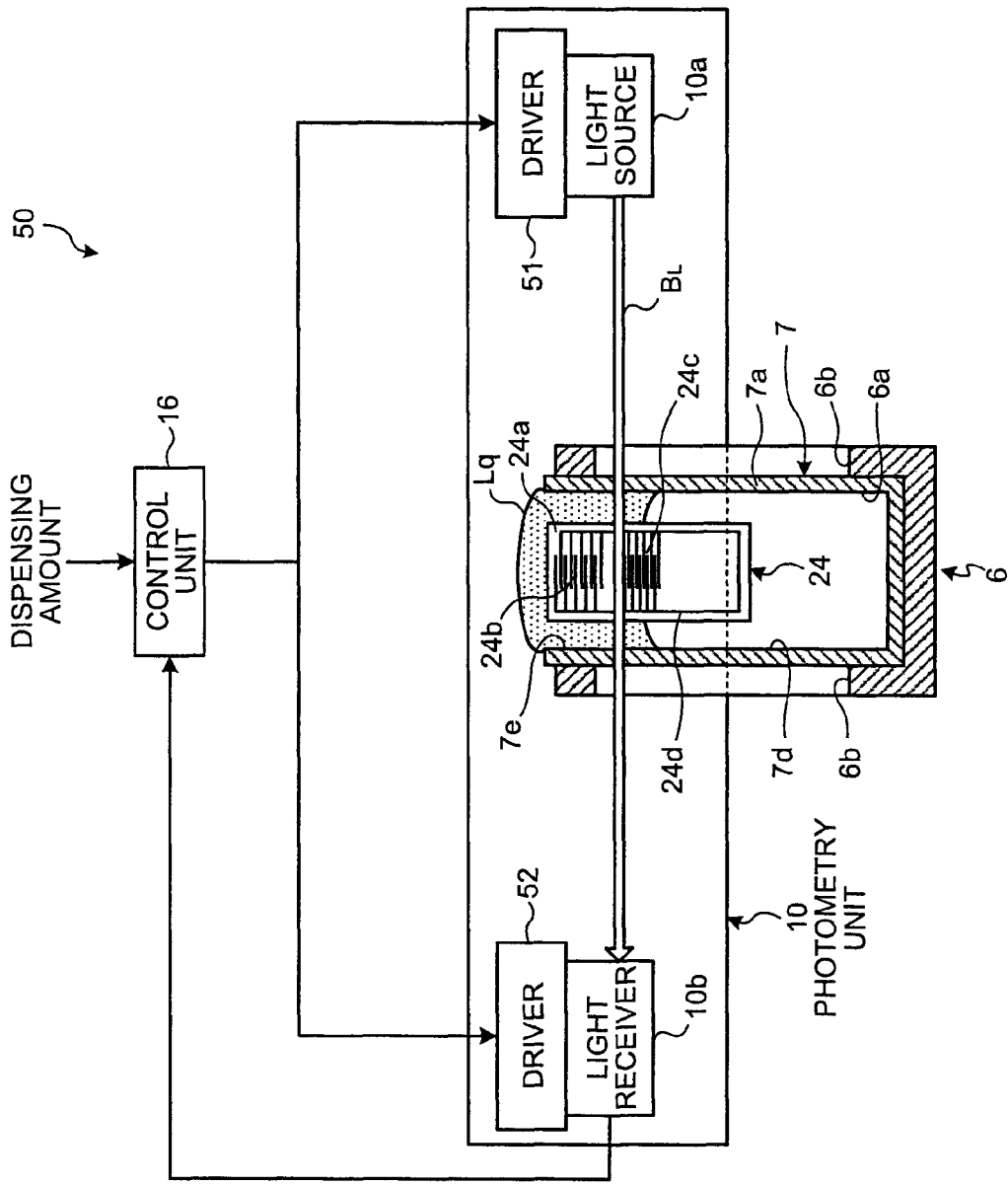
FIG. 45 is a block diagram schematically showing a configuration of the automatic analyzer of a fourth embodiment together with a cross-section of the reaction vessel.

Next, a fourth embodiment of the analyzer of the present invention will be described in detail with reference to the drawings. In the automatic analyzer of the first embodiment, the photometric positions of the light source and the light receiver of the photometry unit have been controlled collectively by one drive means. On the other hand, in the automatic analyzer of the fourth embodiment, the photometric positions of the light source and the light receiver are independently controlled by independent drive means. FIG. 45 is a schematic view showing a schematic configuration of the automatic analyzer of the fourth embodiment together with the cross section of the reaction vessel.

In the automatic analyzer 50, a light source 10a and a light receiver 10b are provided on the driver 51 and the driver 52, respectively, such that the vertical position (photometric position) thereof is controllable, regarding the photometry unit 10 provided on the positions radially facing each other with the concave portion 6a of the reaction wheel 6 interposed therebetween, as shown in FIG. 45. Herein, the drivers 56a and 57a are driven by the control unit 16 to individually control the vertical positions (photometric positions) of the light source 10a and the light receiver 10b. The dispensing amounts of the specimen and the reagent are input from the specimen dispensing mechanism 5 and the reagent dispensing mechanism 12, respectively, to the control unit 16. The control unit 16 obtains in advance the table and the function for deciding the vertical positions, that is, the photometric positions of the light source 10a and the light receiver 10b based on the dispensing amounts, and controls the operations of the drivers 51 and 52 based on the table and the function, thereby controlling the photometric positions.

The automatic analyzer 50 analyzes the liquid held in the reaction vessel 7 in the same manner as the photometric method of the automatic analyzer 1 including the process to control the photometric position at which the photometry of the liquid is performed according to the holding position at which the liquid is held in the reaction vessel 7, and the process to perform the photometry of the liquid at the controlled photometric position.

At this time, as shown in FIG. 45, when the dispensing amount of the liquid Lq is small, since the capacity of the reaction vessel 7 is as extremely small as a few nanoliters (nL) to several tens of microliters (μL), the liquid Lq is held in the vicinity of the opening 7e due to the large effect of the surface tension. Therefore, the control unit 16 obtains the amount of the liquid Lq from the dispensing amounts of the specimen and the reagent input from the specimen dispensing mechanism 5 and the reagent dispensing mechanism 12, respectively, and holds the light source 10a and the light receiver 10b at the initial positions from the table and the function for deciding the photometric position obtained in advance based on the obtained amount of liquid Lq without driving the drivers 51 and 52. Then, the automatic analyzer 50 performs the photometry of the liquid Lq in the vicinity of the opening 7e by the bundle of light BL emitted from the light source 10a, as shown in FIG. 45, in a state in which the light source 10a and the light receiver 10b are held at the initial positions.

Figure 46:
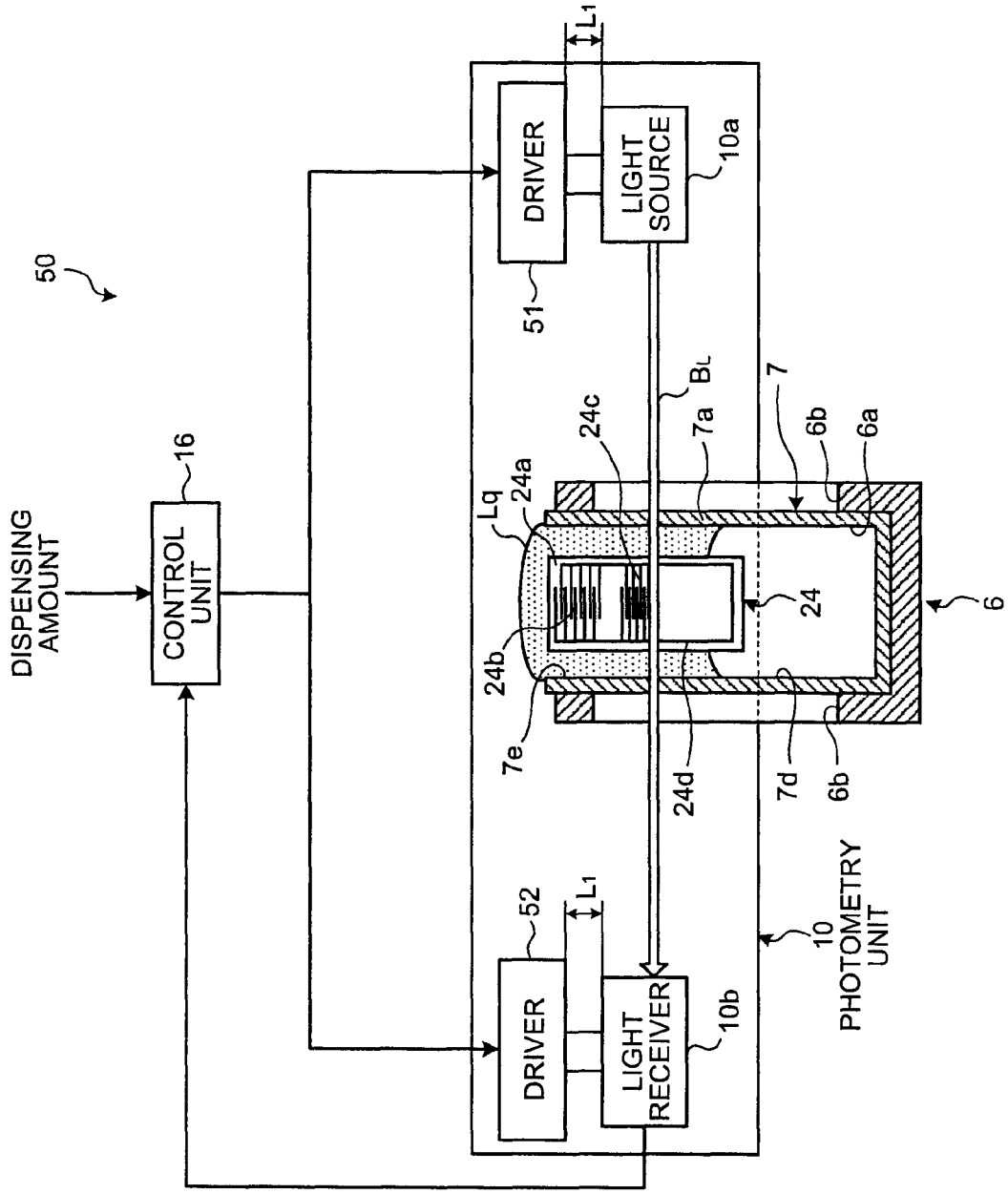
FIG. 46 is a block diagram corresponding to FIG. 45 showing a case in which an amount of the liquid held in the reaction vessel is large.

However, the position at which the reaction vessel 7 holds the liquid Lq including the reagent and the specimen varies according to at least one of the kind or amount of the liquid Lq and the form or the material of the reaction vessel 7. Therefore, when the dispensing amounts of the reagent and the specimen are large and the amount of the liquid Lq is large, for example, as shown in FIG. 46, in the reaction vessel 7, the liquid Lq intrudes halfway into the liquid holding section 7d from the vicinity of the opening 7e.

Therefore, the control unit 16 may perform the photometry of the liquid Lq in the vicinity of the opening 7e, which is the initial position of the photometry unit 10 without controlling the photometric position, or may perform the photometry of the liquid Lq after controlling the photometric position. In this case, the control unit 16 reads the photometric position stored in advance based on the dispensing amount signals regarding the dispensing amounts of the specimen and the reagent input from the specimen dispensing mechanism 5 and the reagent dispensing mechanism 12, respectively, and moves (lowers) the light source 10a and the light receiver 10b from the initial position thereof to the central portion in the vertical direction of the reaction vessel 7 by means of the drivers 51 and 52, respectively, by a distance L1, thereby controlling the photometric positions. Then, the automatic analyzer 50 performs the photometry of the liquid Lq held in the reaction vessel 7 at the photometric position moved downward by the bundle of light BL emitted from the light source 10a, as shown in FIG. 46.

In this manner, in the automatic analyzer 50 of the fourth embodiment, since the control unit 16 individually controls the position of the light source 10a and the light receiver 10b according to the position of the liquid held in the reaction vessel 7, it is possible to control the photometric positions in accordance with the position of the liquid held in the reaction vessel 7, and this allows for the photometry of the liquid held in the reaction vessel 7 even though the liquid is not introduced to the bottom portion of the reaction vessel as in the conventional analyzer.

Figure 47:
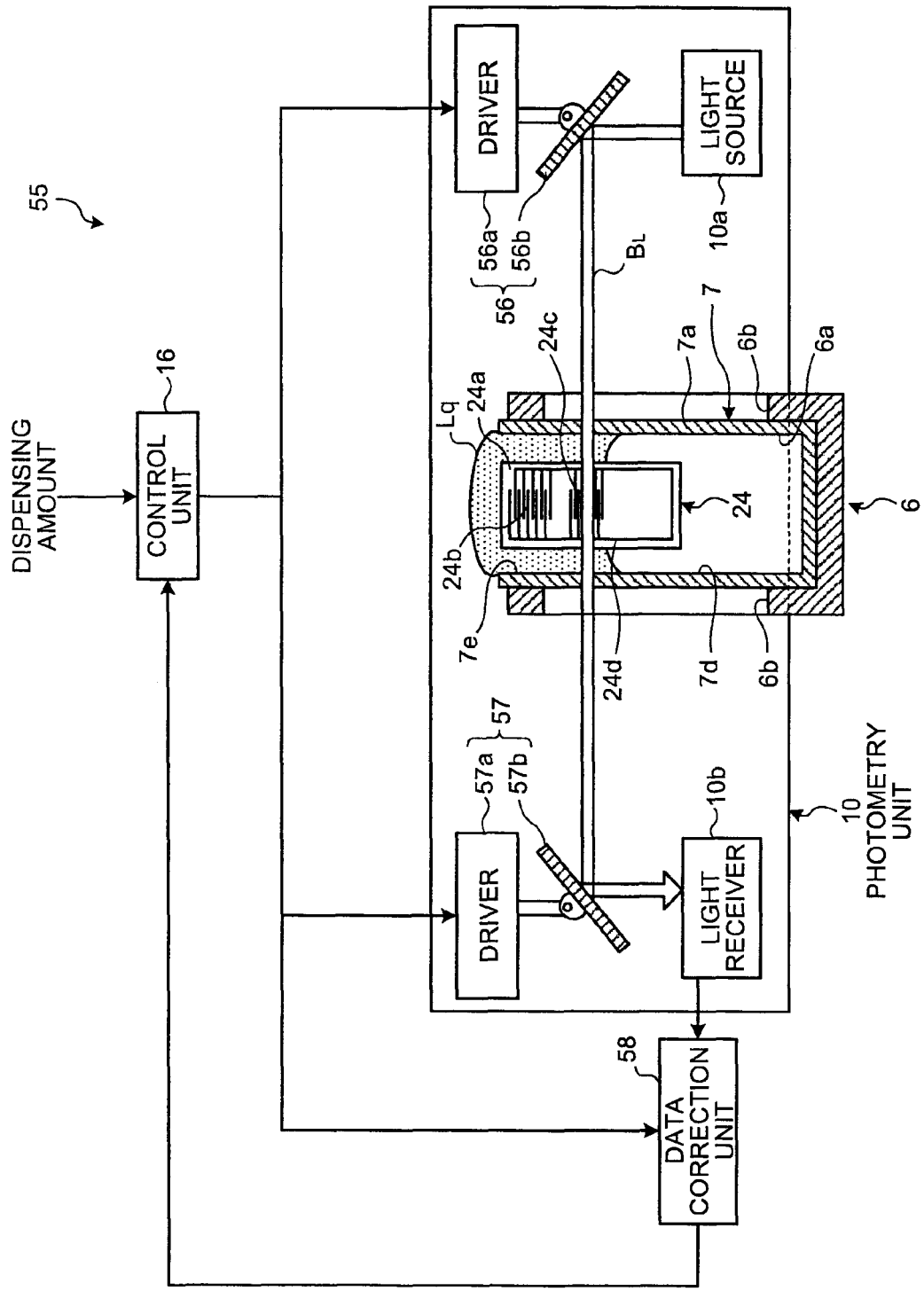
FIG. 47 is a block diagram schematically showing the configuration of the automatic analyzer of a fifth embodiment together with the cross-section of the reaction vessel.

Next, a fifth embodiment of the analyzer of the present invention will be described in detail with reference to the drawings. The automatic analyzer of the fourth embodiment controls the photometric positions of the light source and the light receiver by moving them in the vertical direction by the independent drive means. On the other hand, the automatic analyzer of the fifth embodiment controls the photometric positions of the liquid by independent movable mirrors. FIG. 47 is a schematic view showing a schematic configuration of the automatic analyzer of the fifth embodiment together with the cross section of the reaction vessel.

In an automatic analyzer 55, movable mirrors 56b and 57b are provided on drivers 56a and 57a of drive sections 56 and 57, respectively, such that the angle of inclination is controllable by the drivers 56a and 57a, respectively. Herein, the movable mirrors 56b and 57b are driven by the control unit 16 based on the dispensing amounts of the specimen and the reagent to the reaction vessel 7 by the specimen dispensing mechanism 5 and the reagent dispensing mechanism 12, respectively, input to the control unit 16, and the angles of inclination are controlled. The control unit 16 controls, by the movable mirrors 56ba and 57b, the position at which the bundle of light BL emitted from the light source 10a penetrates the liquid according to the position of the liquid held in the reaction vessel 7.

Therefore, as in the first embodiment, the control unit 16 obtains in advance the table and the function for deciding the position in the vertical direction at which the bundle of light BL penetrates the reaction vessel 7 based on angles of inclination θ1 and θ2 of the movable mirrors 56b and 57b by the drivers 56a and 57a, based on the dispensing amounts of the specimen and the reagent input from the specimen dispensing mechanism 5 and the reagent dispensing mechanism 12 to the reaction vessel 7, and controls the operations of the drivers 56a and 57a based on the table and the function, thereby controlling the photometric position. At this time, due to the inclination of the movable mirrors 56b and 57b, the bundle of light BL penetrating the liquid held in the reaction vessel 7 also inclines, the light path length when penetrating the liquid changes, and also an incident angle θi of the light entering the light receiver 10b, accordingly the incident light amount changes. Therefore, a data correction unit 58 for correcting the light path length and the incident light amount is provided with the automatic analyzer 55.

The microcomputer or the like, for example, is used as the data correction unit 58, which obtains in advance and stores a correction value of the light path length and the incident light amount based on the incident angle of the light entering the reaction vessel 7 and the incident angle θi entering the light receiver 10b from the angles of inclination of the movable mirrors 56b and 57b input by the control unit 16 to the drivers 56a and 57a based on the dispensing amount of the liquid. The data correction unit 58 reads the correction values of the light path length and the incident light amount when the angles of inclination θ1 and θ2 of the movable mirrors 56b and 57b are input from the control unit 16, and outputs the values to the control unit 16. The control unit 16 utilizes the correction values to correct the light absorbance by the photometry unit 10.

The automatic analyzer 55 analyzes the liquid held in the reaction vessel 7 in the same manner as the photometric method of the automatic analyzer 1 including the process to control the photometric position at which the photometry of the liquid is performed according to the holding position at which the liquid is held in the reaction vessel 7, and the process to perform the photometry of the liquid at the controlled photometric position.

At this time, as shown in FIG. 47, when the dispensing amount of the liquid Lq is small, since the capacity of the reaction vessel 7 is as extremely small as a few nanoliters (nL) to several tens of microliters (μL), the liquid Lq is held in the vicinity of the opening 7e due to the large effect of the surface tension. Therefore, the control unit 16, which has obtained the amount of the liquid Lq from the dispensing amounts of the specimen and the reagent input from the specimen dispensing mechanism 5 and the reagent dispensing mechanism 12, respectively, holds the movable mirrors 56b and 57b at the initial positions from the table and the function obtained in advance based on the amount of the obtained liquid Lq without driving the drivers 56a and 57a. Then, the automatic analyzer 55 performs the photometry of the liquid Lq in the vicinity of the opening 7e by the bundle of light BL emitted from the light source 10a, as shown in FIG. 47, in a state in which the movable mirrors 56b and 57b are held at the initial positions.

However, the position at which the reaction vessel 7 holds the liquid Lq including the reagent and the specimen varies according to at least one of the kind or the amount of the liquid Lq and the form or the material of the reaction vessel 7. Therefore, when the dispensing amounts of the reagent and the specimen are large and the amount of the liquid Lq is large, for example, as shown in FIG. 48, in the reaction vessel 7, the liquid Lq might intrude halfway into the liquid holding section 7d from the vicinity of the opening 7e.

Figure 48:
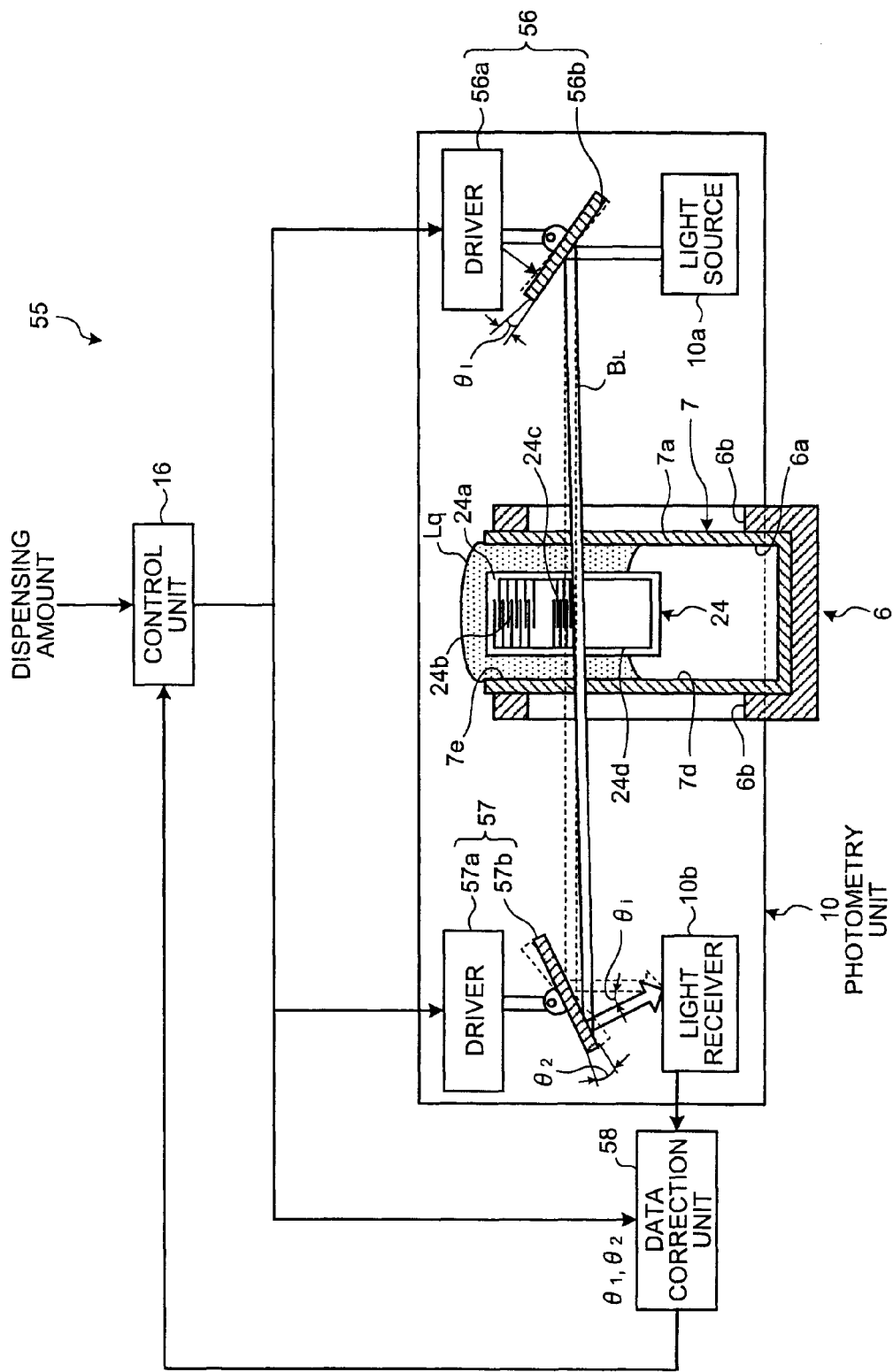
FIG. 48 is a block diagram corresponding to FIG. 47 showing a case in which an amount of the liquid held in the reaction vessel is large.

Therefore, when the liquid Lq intrudes halfway into the liquid holding section 7d from the vicinity of the opening 7e, as shown in FIG. 48, the control unit 16 may perform the photometry of the liquid Lq at the initial position of the photometry unit 10 without controlling the photometric position, or may perform the photometry of the liquid Lq after controlling the photometric position. In this case, the control unit 16 reads the photometric position stored in advance based on the dispensing amount signals regarding the dispensing amounts of the specimen and the reagent input from the specimen dispensing mechanism 5 and the reagent dispensing mechanism 12, respectively, and inclines the movable mirrors 56b and 57b from the initial positions thereof by the angles of inclination θ1 and θ2 by means of the drivers 56 and 57a, respectively. Thereby, the control unit 16 lowers the position in the vertical direction at which the bundle of light BL penetrates the reaction vessel 7, thereby controlling the photometric position. Then, the automatic analyzer 55 performs the photometry of the liquid Lq held in the reaction vessel 7 at the photometric position moved downward by the bundle of light BL emitted from the light source 10a, as shown in FIG. 47.

In this manner, in the automatic analyzer 55 of the fifth embodiment, since the control unit 16 controls the photometric position by inclining the movable mirrors 56b and 57b according to the position of the liquid held in the reaction vessel 7, it is possible to control the photometric position in accordance with the position of the liquid held in the reaction vessel 7, and this allows for the photometry of the liquid held in the reaction vessel 7 even though the liquid is not introduced to the bottom portion of the reaction vessel as in the conventional analyzer.

Herein, the automatic analyzer 55 may change the positions of the movable mirrors 56b and 57b in the vertical direction from the initial positions thereof in place of inclining the movable mirrors 56b and 57b by the drivers 56a and 57a, respectively. By thus configuring, the automatic analyzer 55 does not require to be provided with the data correction unit 58 because the light path length and the incident light amount when the bundle of light BL penetrates the liquid do not change.

Sixth Embodiment

Figure 49:
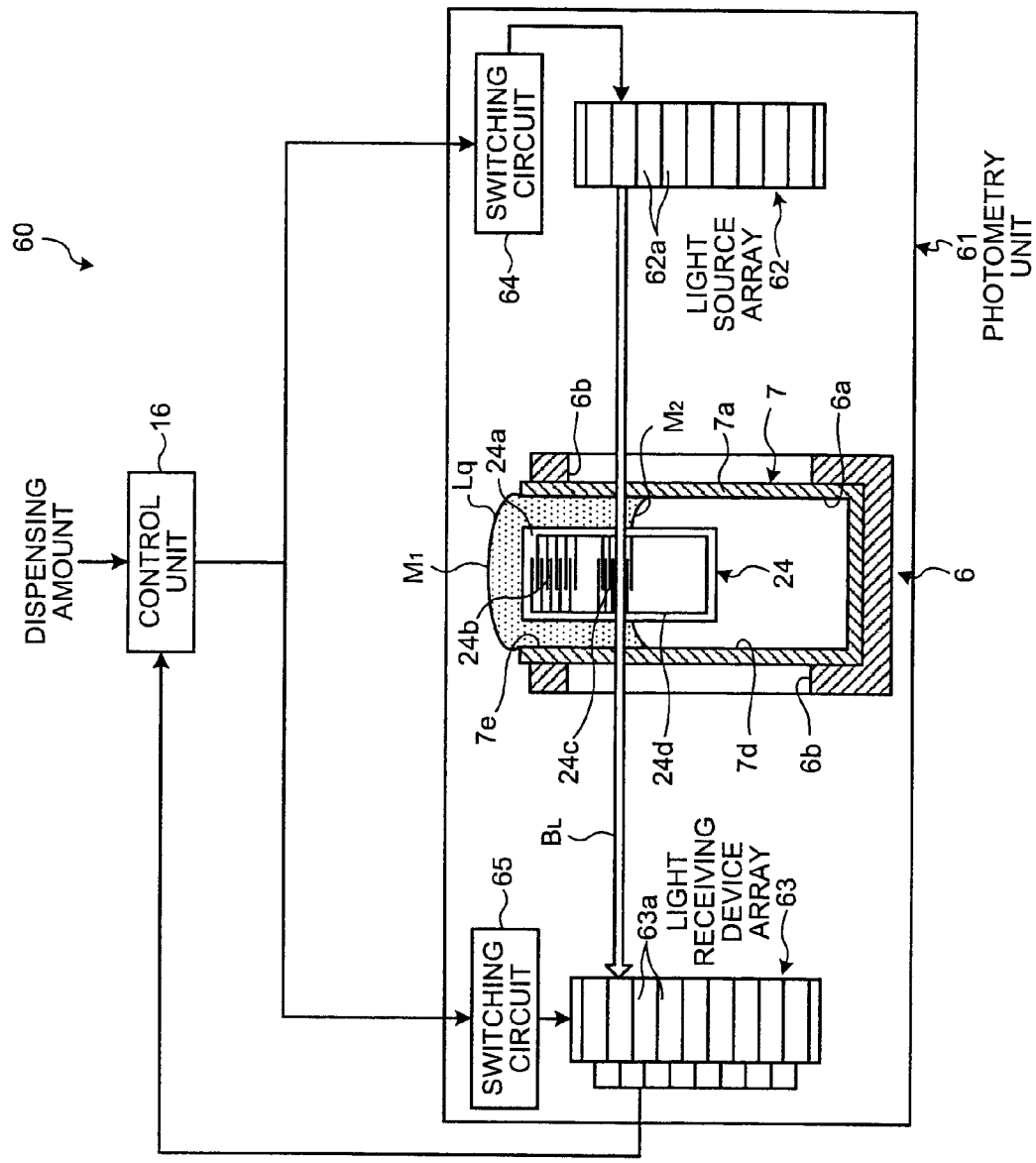
FIG. 49 is a block diagram schematically showing the configuration of the automatic analyzer of a sixth embodiment together with the cross-section of the reaction vessel.

Next, a sixth embodiment of the analyzer of the present invention will be described in detail with reference to the drawings. The automatic analyzer of the fifth embodiment performs the photometry of the bundle of light emitted from the single light source by the single light receiver. On the other hand, the automatic analyzer of the sixth embodiment performs the photometry of the bundle of light emitted from a plurality of light sources by a plurality of light receivers. FIG. 49 is a schematic view showing a schematic configuration of the automatic analyzer of the sixth embodiment together with the cross section of the reaction vessel.

In an automatic analyzer 60, a photometry unit 61 has a light source array 62 formed of a plurality of LEDs 62a and a light receiving device array 63 formed of a plurality of light receiving devices 63a, as shown in FIG. 49. The automatic analyzer 60 forms the position detector of the control unit 16 and the photometry unit 61, and the control unit 16 becomes the detecting section for detecting the position of the liquid held in the reaction vessel 7 based on photometric data of the light receiving device array 63. At this time, a plurality of LEDs 62a and a plurality of light receiving devices 63a are arranged along the vertical direction orthogonal to the gas-liquid interfaces M1 and M2 of the liquid Lq held in the reaction vessel 7. The automatic analyzer 60 sequentially lights the LEDs 62a by switching the control signal output from the control unit 16 by a switch circuit 64 and outputting the signal to the light source array 62. Concurrently, the automatic analyzer 60 switches the control signal output from the control unit 16 by the switch circuit 65 to sequentially receive the analytical light emitted from the LEDs 62a by the corresponding light receiving device 63a in the light receiving device array 63, thereby performing the photometry and the position detection of the liquid Lq held in the reaction vessel 7. The photometric data received by each light receiving device 63a is output to the control unit 16.

At this time, the control unit 16 obtains in advance the table and the function for deciding the position, that is, the photometric position of the liquid Lq, based on the dispensing amounts of the specimen and the reagent input from the specimen dispensing mechanism 5 and the reagent dispensing mechanism 12, respectively, and sequentially switches the LED 62a and the light receiving device 63a based on the table and the function, thereby controlling the photometric position. Then, the control unit 16 compares the photometric data in which the light amount due to the absorption by the liquid Lq is small and the photometric data in which the light amount is large because the light absorption is small due to the absence of the liquid Lq, in the photometric data input from each light receiving device 63a, and detects the position of the light receiving device 63a outputting the photometric data in which the light amount is small as the position of the liquid and sets the photometric data of the light receiving device 63a in which the light receiving amount is the smallest as the measurement amount of the analytical light penetrated the liquid Lq. In this case, the number of light receiving devices 63a at the position at which the liquid Lq exists may be single or plural depending on the amount of the liquid. Also, it is possible not only to control the photometric position by sequentially switching the LED and the light receiving device but also to obtain in advance the position at which the liquid Lq is held to select the LED and the light receiving device to be driven according to the position. By thus configuring, it becomes possible to control the photometric position.

The automatic analyzer 60 analyzes the liquid held in the reaction vessel 7 in the manner similar to the photometric method of the automatic analyzer 1 including the process to control the photometric position for performing the photometry of the liquid according to the holding position at which the liquid is held in the reaction vessel 7, and the process to perform the photometry of the liquid at the controlled photometric position.

At this time, as shown in FIG. 49, when the dispensing amount of the liquid Lq is small, since the capacity of the reaction vessel 7 is as extremely small as a few nanoliters (nL) to several tens of microliters (μL), the liquid Lq is held in the vicinity of the opening 7e due to the large effect of the surface tension. Therefore, the control unit 16 obtains the amount of the liquid Lq from the dispensing amounts of the specimen and the reagent input from the specimen dispensing mechanism 5 and the reagent dispensing mechanism 12, respectively, and sequentially switches the LED 62a and the light receiving device 63a based on the table and the function for deciding the photometric position obtained in advance based on the obtained amount of the liquid Lq, thereby performing the photometry of the liquid Lq in the vicinity of the opening 7e while controlling the photometric position.

However, the position at which the reaction vessel 7 holds the liquid Lq including the reagent and the specimen varies according to at least one of the kind or the amount of the liquid Lq and the form or the material of the reaction vessel 7. Therefore, for example, there might occur a case in which the dispensing amounts of the reagent and the specimen are large and the amount of the liquid Lq is large, so that the liquid Lq intrudes halfway into the liquid holding section 7d from the vicinity of the opening 7e, or a case in which the liquid Lq of which amount is small intrudes halfway into the liquid holding section 7d from the vicinity of the opening 7e.

In this case, the control unit 16 may perform the photometry of the liquid Lq in the vicinity of the opening 7e, which is the initial position of the photometry unit 10 without controlling the photometric position, or may perform the photometry of the liquid Lq while controlling the photometric position by sequentially switching the LED 62a and the light receiving device 63a. Also, in a case in which the liquid Lq of which amount is small intrudes into the liquid holding section 7d, it is understood that the liquid does not exist in the vicinity of the opening 7e from the photometric data in the vicinity of the opening 7e. Therefore, in the automatic analyzer 60, the control unit 16 performs the photometry of the liquid Lq in the vicinity of the opening 7e while controlling the photometric position by sequentially switching the LED 62a and the light receiving device 63a located in the range decided based on the table and the function, from the position at which the presence of the liquid is detected and the information of the dispensing amount.

In this manner, in the automatic analyzer 60 of the sixth embodiment, since the control unit 16 sequentially switches the LED 62a and the light receiving device 63a according to the position of the liquid held in the reaction vessel 7, the photometric position may be controlled in accordance with the position of the liquid held in the reaction vessel 7, and this allows for the photometry of the liquid held in the reaction vessel 7 even though the liquid is not introduced to the bottom portion of the reaction vessel as in the conventional analyzer.

Especially, in the automatic analyzer 60 of the sixth embodiment, since the position detector of the present invention is formed of the photometry unit 61 and the control unit 16, which becomes the detecting section for detecting the position of the liquid held in the reaction vessel 7, the position of the liquid held in the reaction vessel 7 is detected, and the control unit 16 sequentially switches the LED 32a and the light receiving device 33a according to the detected position of the liquid, it is possible to perform the photometry of the liquid by the photometry unit 31 at the position of the liquid held in the reaction vessel 7. In this manner, the position detector described in the sixth embodiment may detect the position of the liquid held in the reaction vessel 7 with a simple configuration, and the automatic analyzer 60 may perform the photometry of the liquid at the position of the liquid held in the reaction vessel 7. Also, as in the first embodiment, since the position of the liquid may be detected from outside the reaction vessel 7 without contacting the liquid in the reaction vessel 7, the position detector described in the sixth embodiment may prevent another substance from being mixed into the reaction vessel 7 when used in the automatic analyzer 60.

Also, the automatic analyzer 60 does not use the driver for driving movable parts such as the movable mirrors 56b and 57b as in the automatic analyzer 55 of the fifth embodiment, so that it is possible to cut the process of reducing the noise received by the light source 66 and the light receiving device array 63 and the reference photometry.

Figure 50:
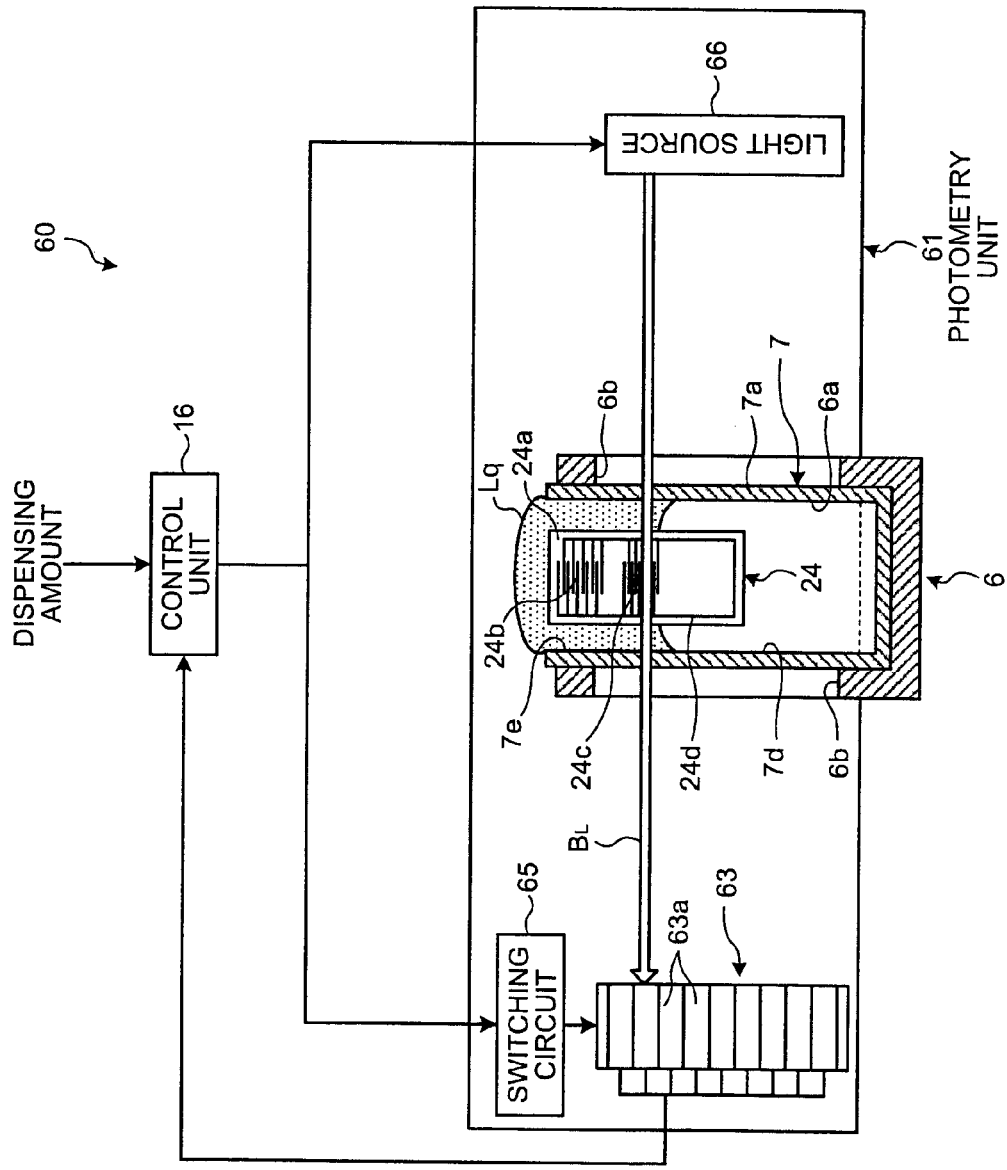
FIG. 50 is a block diagram schematically showing a first modified example of the automatic analyzer of the sixth embodiment together with the cross-section of the reaction vessel.

Herein, as one modification of the fifth embodiment, the automatic analyzer 60 may have a single light source 66 in place of the light source array 62 as shown in FIG. 50, and switch the control signal output from the control unit 16 by the switch circuit 65. Then, the photometry of the liquid Lq is performed in the vicinity of the opening 7e of the reaction vessel 7 by sequentially receiving the analytical light emitted from the light source 66 by a plurality of light receiving devices 63a. Thereby, the control unit 16 may detect the holding position of the liquid from the photometric data output from each of the light receiving devices 63a together with the photometry. Herein, the control unit 16 selects the light receiving device 63a existing at the position based on the dispensing amounts of the specimen and the reagent input from the specimen dispensing mechanism 5 and the reagent dispensing mechanism 12, respectively, when selecting a specific light receiving device 63a to be used in the photometry. Accordingly, the automatic analyzer 60 may perform the photometry of the liquid Lq while controlling the photometric position by the light receiving device array 63 in accordance with the position of the liquid Lq held in the reaction vessel 7 by selecting the specific light receiving device 63a by the control unit 16 even when the amount of the liquid held in the reaction vessel 7 is large. Meanwhile, the single light source is provided on an emitting surface of the light source such that a lens for parallelizing measurement light corresponds to each component of a facing light receiving device.

On the other hand, as another modification of the fifth embodiment, the automatic analyzer 60 may sequentially light a plurality of LEDs 62a of the light source array 62 by using a single light receiving device 67 in place of the light receiving device array 63 and by switching the control signal output from the control unit 16 by the switch circuit 64 as shown in FIG. 51. In addition, it is possible to perform the photometry of the liquid Lq in the vicinity of the opening 7e of the reaction vessel 7 by sequentially receiving the analytical light emitted from each LED 62a by the light receiving device 67. Thereby, the control unit 16 may detect the holding position of the liquid by specifying the LED 62a, which has emitted the analytical light having penetrated the liquid Lq from a plurality of photometric data output from the light receiving device 67. Herein, the control unit 16 selects the LED 62a existing at the position based on the dispensing amounts of the specimen and the reagent input from the specimen dispensing mechanism 5 and the reagent dispensing mechanism 12, respectively, when selecting the LED 62a to be lit. Accordingly, the automatic analyzer 60 may perform the photometry of the liquid Lq while controlling the photometric position by the light source array 62 in accordance with the position of the liquid Lq held in the reaction vessel 7, by selecting the LED 62a to be lit by the control unit 16 even when the amount of the liquid held in the reaction vessel 7 is large.

As is clear from the above description, according to the modified examples 1 and 2, it is possible to reduce the number of components of the light source, the light receiving section and the switch circuit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An analyzer for measuring optical characteristics of liquid, comprising:
   a vessel for holding the liquid in a state of having at least two gas-liquid interfaces, wherein the cross sectional area of the vessel is approximately equal to each of the respective areas of the at least two gas-liquid interfaces; and
   a photometric unit that measures the optical characteristics of the liquid held in the vessel.

2. The analyzer according to claim 1, wherein in the vessel, a sum of a vertical component of surface tension acting from the liquid on an entire circumference of an inner wall of the vessel and force acting vertically upward from gas in the vessel on the liquid is not less than weight of the liquid, when the at least two gas-liquid interfaces are arranged up and down in the vertical direction.

3. The analyzer according to claim 1, wherein the photometric unit measures the optical characteristics of the liquid in a portion enclosed by the vessel between the at least two gas-liquid interfaces.

4. The analyzer according to claim 1, wherein the photometric unit measures the optical characteristics of the liquid along a direction orthogonal to a moving direction of the liquid held in the vessel.

5. The analyzer according to claim 1, further comprising:
   a dispensing unit that dispenses the liquid to the vessel; and
   a stirring unit that stirs dispensed liquid, wherein
   another liquid is dispensed and stirred and the optical characteristics thereof are measured at a position at which the liquid is held in the vessel.

6. The analyzer according to claim 1, wherein the photometric unit measures the optical characteristics of the liquid in a case in which at least one gas-liquid interface exists outside the vessel.

7. The analyzer according to claim 1, wherein the photometric unit measures the optical characteristics of the liquid in a case in which all of the gas-liquid interfaces, which the liquid has, exist in the vessel.

8. The analyzer according to claim 1, further comprising a control unit that controls a photometric position when measuring the optical characteristics of the liquid.

9. The analyzer according to claim 8, wherein the control unit controls the photometric position according to at least one of a kind or an amount of the liquid and a form or a material of the vessel.

10. A vessel used in an analyzer for measuring optical characteristics of liquid, comprising:
    an opening for introducing the liquid; and
    a liquid holding section for holding the liquid introduced from the opening in a state of having at least two gas-liquid interfaces,
    wherein the cross sectional area of the vessel is approximately equal to each of the respective areas of the at least two gas-liquid interfaces.

11. The vessel according to claim 10, wherein in the vessel, a sum of a vertical component of surface tension acting from the liquid on an entire circumference of an inner wall of the vessel and force acting vertically upward from gas in the vessel on the liquid is not less than weight of the liquid in a case in which the at least two gas-liquid interfaces are arranged up and down in the vertical direction.

* * * * *